(12) United States Patent
Fish et al.

(10) Patent No.: US 12,201,372 B2
(45) Date of Patent: *Jan. 21, 2025

(54) LESION PREDICTION BASED IN PART ON TISSUE CHARACTERIZATION

(71) Applicant: St. Jude Medical, Cardiology Division, Inc., St. Paul, MN (US)

(72) Inventors: Jeffrey M. Fish, Maple Grove, MN (US); Lynn E. Clark, Knoxville, TN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/527,985

(22) Filed: Dec. 4, 2023

(65) Prior Publication Data
US 2024/0189033 A1 Jun. 13, 2024

Related U.S. Application Data

(63) Continuation of application No. 15/583,519, filed on May 1, 2017, now Pat. No. 11,883,106.
(Continued)

(51) Int. Cl.
*A61B 34/10* (2016.01)
*A61B 18/12* (2006.01)
(Continued)

(52) U.S. Cl.
CPC .............. *A61B 34/10* (2016.02); *A61B 18/12* (2013.01); *A61B 18/1206* (2013.01); *A61B 18/1492* (2013.01); *A61B 34/25* (2016.02); *A61B 2018/00577* (2013.01); *A61B 2018/0066* (2013.01); *A61B 2018/00779* (2013.01); *A61B 2018/00875* (2013.01); *A61B 2090/065* (2016.02)

(58) Field of Classification Search
CPC ......... A61B 34/10; A61B 34/25; A61B 18/12; A61B 18/1206; A61B 18/1492; A61B 2090/065; A61B 2018/00577; A61B 2018/0066; A61B 2018/00779; A61B 2018/00875
See application file for complete search history.

(56) References Cited

U.S. PATENT DOCUMENTS

| 5,604,688 A | 2/1997 | Chu et al. |
| 7,263,397 B2 | 8/2007 | Hauck et al. |

(Continued)

*Primary Examiner* — Eun Hwa Kim
*Assistant Examiner* — Catherine Premraj
(74) *Attorney, Agent, or Firm* — Wiley Rein LLP

(57) ABSTRACT

A method for determining a predicted lesion size formed in a tissue by receiving or calculating a measure of contact force between the electrode and the tissue, determining a tissue characterization, and calculating the predicted lesion size using both the measure of contact force and the tissue characterization. A system comprising an electronic control unit configured to receive or determine a measure of contact force between the electrode and the tissue, characterize the tissue based on both the measure of impedance and the measure of contact force, and cause the tissue characterization to be either (a) presented to a user, or (b) applied to calculate a metric and cause the metric to be presented to the user.

13 Claims, 13 Drawing Sheets

Related U.S. Application Data

(60) Provisional application No. 62/331,398, filed on May 3, 2016.

(51) Int. Cl.
  *A61B 18/14* (2006.01)
  *A61B 34/00* (2016.01)
  *A61B 18/00* (2006.01)
  *A61B 90/00* (2016.01)

(56) References Cited

U.S. PATENT DOCUMENTS

| | | |
|---|---|---|
| 8,403,925 B2 | 3/2013 | Miller et al. |
| 8,454,589 B2 | 6/2013 | Curtis et al. |
| 9,237,920 B2 | 1/2016 | Leo et al. |
| 2007/0060847 A1 | 3/2007 | Leo et al. |
| 2007/0112342 A1 | 5/2007 | Pearson et al. |
| 2008/0009750 A1 | 1/2008 | Aeby et al. |
| 2009/0030477 A1 | 1/2009 | Jarrad |
| 2009/0171345 A1 | 7/2009 | Miller et al. |
| 2010/0298826 A1 | 11/2010 | Leo |
| 2011/0144524 A1 | 6/2011 | Fish et al. |
| 2011/0264000 A1 | 10/2011 | Paul et al. |
| 2011/0270046 A1 | 11/2011 | Paul et al. |
| 2012/0209260 A1 | 8/2012 | Lambert et al. |
| 2013/0226169 A1* | 8/2013 | Miller ............... A61B 18/1233 606/34 |
| 2014/0364715 A1 | 12/2014 | Hauck |
| 2014/0364848 A1 | 12/2014 | Heimbecher |

* cited by examiner

LESION PREDICTION BASED IN PART ON TISSUE CHARACTERIZATION

CROSS-REFERENCE TO RELATED APPLICATIONS

This application is a continuation of U.S. application Ser. No. 15/583,519, filed 1 May 2017 ("the '519 application"), now U.S. Pat. No. 11,883,106, which claims the benefit of U.S. provisional application No. 62/331,398, filed 3 May 2016 ("the '398 provisional"). The '519 application and the '398 provisional are hereby incorporated by reference as though fully set forth herein.

BACKGROUND a. Technical Field

The instant disclosure relates to tissue characterization and lesion prediction/assessment, including, for example, estimation of lesion size based in part on tissue morphology characterization.

b. Background Art

Atrial fibrillation is a common cardiac arrhythmia involving the two upper chambers (atria) of the heart. In atrial fibrillation, disorganized electrical impulses that originate in the atria and pulmonary veins overwhelm the normal electrical impulses generated by the sinoatrial node, leading to conduction of irregular impulses to the ventricles that generate the heartbeat. Atrial fibrillation can result in poor contraction of the atria that can cause blood to recirculate in the atria and form clots. Thus, individuals with atrial fibrillation have a significantly increased risk of stroke. Atrial fibrillation can also lead to congestive heart failure or, in extreme cases, death.

Common treatments for atrial fibrillation include medications or synchronized electrical cardioversion that convert atrial fibrillation to a normal heart rhythm. Surgical-based therapies have also been developed for individuals who are unresponsive to or suffer serious side effects from more conventional treatments. The surgical techniques include making incisions in the right and left atria to block propagation of the abnormal electrical impulse around the atrial chamber.

Catheter-based contact ablation techniques have evolved as a minimally invasive alternative to surgical-based techniques, and also as an alternative for individuals who are unresponsive to or suffer serious side effects from more conventional treatments (e.g., medications). Contact ablation techniques involve the ablation of groups of cells near the pulmonary veins where atrial fibrillation is believed to originate, or the creation of extensive lesions to break down the electrical pathways from the pulmonary veins located on the posterior wall of the left atrium. Methods of energy delivery include radiofrequency, microwave, cryothermy, laser, and high intensity ultrasound. The contacting probe is placed into the heart via a catheter that enters a vein in the groin or neck and is routed to the heart, thus negating the need for an incision in the heart wall from the outside. The probe is then placed in contact with the posterior wall of the left atrium and energized to locally ablate the tissue and electrically isolate the pulmonary veins from the left atrium. The advantages of catheter-based contact ablation techniques have been recognized to include a minimally invasive surgical access, thus reducing risks of infection, and reduced recuperation times.

Where complete electrical isolation is desired, the objective of the contact ablation technique is to form a continuous "ablation line" or "isolation line" of ablated tissue between the left atrium and the pulmonary veins. At least two different approaches for achieving an isolation line have been developed: point contact ablation where the energy delivery is from a head end of the contacting probe generally in line with a longitudinal axis of the contacting probe; and linear contact ablation where the energy delivery is from a side of the contacting probe and generally transverse to the longitudinal axis of the contacting probe.

A concern with catheter-based contact ablation techniques is the post-operative recurrence of atrial fibrillation, believed to be caused by electrical reconnection of one or more pulmonary veins across the isolation line to the atrial tissue. The sites along the isolation line where this type of electrical reconnection occurs are referred to as "isolation gaps" or simply "gaps." Gaps can occur due to suboptimal catheter contact force during ablation for either point contact ablation or linear contact ablation techniques or in areas that were missed. The left anterior wall is often a difficult area to achieve stable contact during pulmonary vein isolation resulting in higher incidence of local isolation gaps.

One approach to identifying or predicting possible isolation gaps has been to make electrical continuity measurements across the isolation line after the isolation line has been created. While this approach may work in some cases for linear contact ablation techniques, it is generally not effective for point contact ablation techniques because it requires too much time and too many continuity measurements in order to establish a relatively high confidence in the ability to predict whether there will or will not be isolation gaps as a result of incomplete lesion formations during the ablation process of creating the isolation. In addition, it has been found that intra-operative continuity measurements of the isolation line may not be an accurate predictor of the recurrence of atrial fibrillation as the tissue properties of the lesion just after ablation can change over time and may not be representative of the final lesions associated with the isolation line.

The predictability of lesion formation in the context of point contact ablation techniques has been enhanced with the advent of force sensing ablation catheters. The ability to incorporate the contact forces utilized in point-to-point ablation procedures has led to new systems and processes directed to the prediction of ablation size. U.S. Patent Application Publication No. 2010/0298826, now U.S. Pat. No. 8,641,705, assigned to the assignee of the instant matter, discloses the use of a force-time integral for real time estimation of lesion size in catheter-based ablation systems. U.S. Patent Application Publication No. 2010/0298826 is hereby incorporated by reference as though fully set forth herein.

Ablation therapy may be used to treat various conditions afflicting the human anatomy. One such condition that ablation therapy finds a particular application is in the treatment of atrial arrhythmias, for example. When tissue is ablated, or at least subjected to ablative energy generated by an ablation generator and delivered by ablation catheter, lesions form in the tissue. More particularly, electrodes mounted on or in ablation catheters are used to create tissue necrosis in cardiac tissue to correct conditions such as atrial arrhythmia (including, but not limited to, ectopic atrial tachycardia, atrial fibrillation, and atrial flutter). Arrhythmia can create a variety of dangerous conditions including irregular heart rates, loss of synchronous atrioventricular contractions and stasis of blood flow which can lead to a variety of ailments and even death. It is believed that the primary cause of atrial arrhythmia is stray electrical signals within the left or right atrium of the heart. The ablation catheter imparts ablative energy (e.g., radiofrequency energy, cryothermy, lasers, chemicals, high-intensity focused ultrasound, etc.) to cardiac tissue to create a lesion in the cardiac tissue. This lesion disrupts undesirable electrical pathways and thereby limits or prevents stray electrical signals that lead to arrhythmias.

One challenge with ablation procedures is in the assessment of the lesion formation as a result of the application of ablative energy to the tissue. For example, it may be difficult to determine whether a particular area of tissue has been ablated or not, the extent to which ablated tissue has been ablated, whether a lesion line is continuous or has gaps therein, etc. Lesion formation has typically been assessed using any one of a number of different empirical techniques.

One such technique depends on a subjective sense for catheter contact combined with RF power settings, for example, and the duration the electrode spends in contact with the tissue. Another technique employs temperature sensing. A further method relies on ablation catheter electrogram signals. RF ablated myocardium demonstrates poor depolarization wavefront conduction and thus local electrogram amplitude reduction and morphology changes are sometimes, but not consistently, observed. Accordingly, the assessment of lesion formation has ordinarily no direct objective basis.

The foregoing discussion is intended only to illustrate the present field and should not be taken as a disavowal of claim scope.

BRIEF SUMMARY

Various embodiments herein provide a system for lesion assessment based on impedance and force. In at least one embodiment, a system can include an electronic control unit (ECU) configured to receive a measurement of impedance between an electrode and tissue, and a measurement of a contact force between the electrode and the tissue. The system presents a tissue characterization or calculates a metric to be presented to the user that represents the tissue characterization. The system may include a fraction representing the ratio between the impedance and the contact force. The system may include a monitor to display the tissue characterization. The ECU may also generate a map or model of the tissue to be displayed. The ECU may also use the tissue characterization to calculate a metric that is representative of a lesion in the tissue. The ECU may be configured to calculate an expected lesion size using a measure of contact force and a measure of energy applied to the electrode. The system may include a signal generator and an optical signal source.

Various embodiments herein provide a method of lesion assessment based on impedance and force. In at least one embodiment, a method can include an ECU that presents tissue characterization or calculates a metric to be presented to the user that represents the tissue characterization. The method may include the use of a fraction representing the ratio between the impedance and the contact force. The method may include an ECU to display the tissue characterization. The method may include the ECU that may also include a map or model of the tissue to be displayed. The method may use the ECU that may also use the tissue characterization to calculate a metric that is representative of a lesion in the tissue. The method may also use an ECU that may be configured to calculate an expected lesion size using a measure of contact force and a measure of energy applied to the electrode. The method may use a signal generator and an optical signal source.

Various embodiments herein provide a system for lesion assessment based on, for example, impedance and force. In at least one embodiment, a system can include an ECU configured to receive a measurement of impedance between an electrode and tissue, and a measurement of a contact force between the electrode and the tissue. The system presents a lesion size (e.g., the lesion depth, width, depth at maximum diameter, volume, or cross-sectional area). The ECU may calculate or estimate the size of the lesion based upon, for example, a lesion size index (LSI) value (which itself may be based upon RF power, force, and time) and the ratio of at least one of at least one of the following to contact force: RF generator impedance, an electrical coupling index (ECI) value, resistance between the catheter tip and tissue, or reactance between the catheter tip and tissue. The system may also present the lesion size by including, for example, the lesion depth in a map or model of the tissue and displaying the map or the model for a clinician or the user.

DETAILED DESCRIPTION

The disclosure below generally includes three portions. First, a broad system for performing an ablation procedure and estimating lesion size will be described with respect to FIGS. 1 and 2. Second, the ablation and impedance sensing features of the system of FIG. 2 will be elaborated upon with respect to FIGS. 1-4. Third, tissue morphology characterization and lesion depth estimation using the system of FIG. 2 will be discussed. As part of this third aspect, experimental data demonstrating the efficacy of the methods of tissue morphology characterization and lesion size estimation of the present disclosure will be discussed with reference to FIGS. 5-15.

System for Performing Ablation and Estimating Lesion Size

Figure 1:
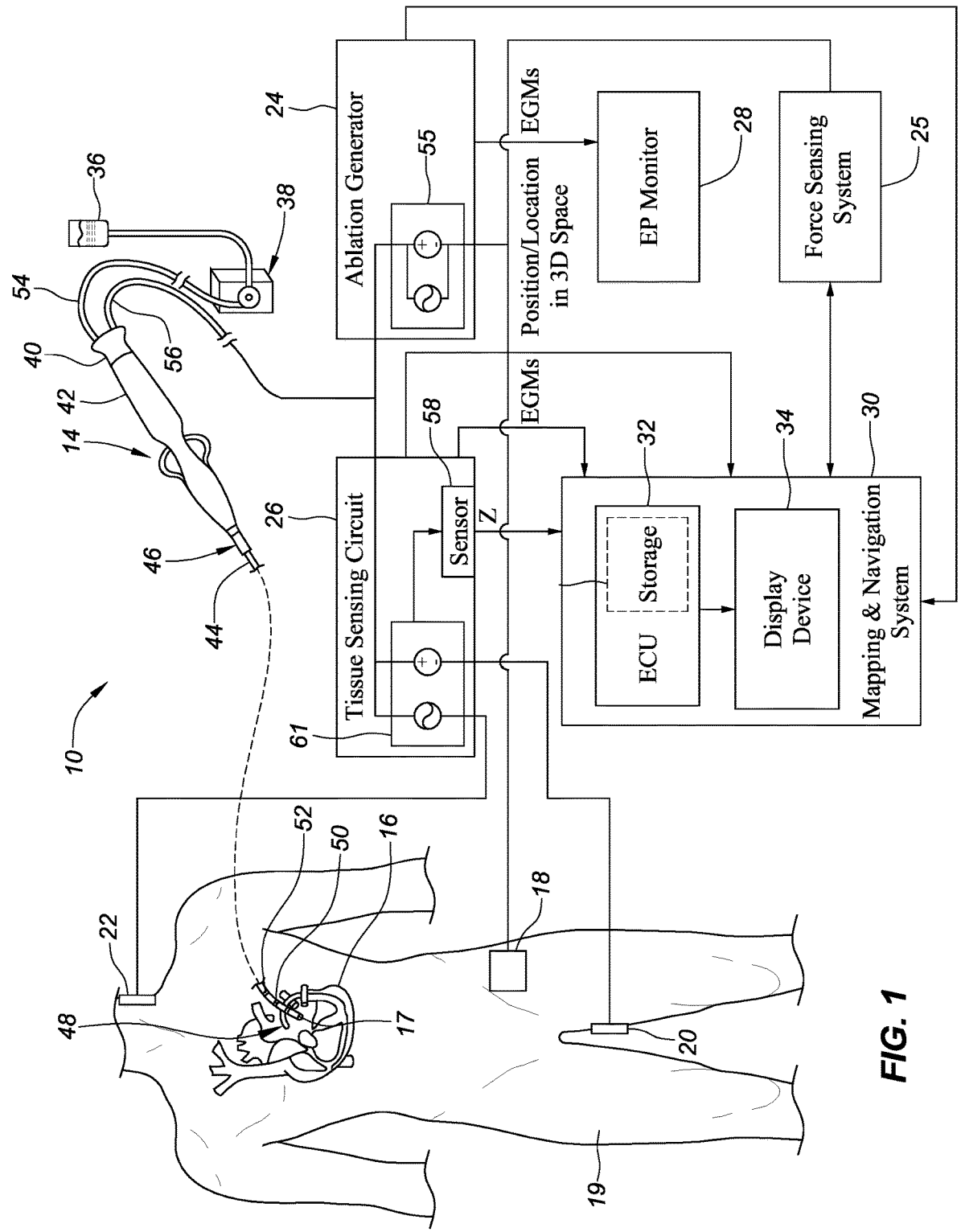
FIG. 1 is a schematic and block diagram view of a system for performing an ablation procedure.

Referring now to the figures, in which like numerals indicate the same or similar elements in the various views, FIG. 1 is a block diagram view of an exemplary embodiment of a system 10 for performing a medical procedure. The system 10 may be used, for example, to perform an ablation procedure on tissue 16 of a patient, such as the heart of the patient. The system 10 may include a mapping and navigation system 30, an ablation generator 24, a force sensing system 25, an impedance sensing system 26, and an elongate medical device 14. The elongate medical device 14 may be, for example only, a catheter, and will be referred to as a catheter for the remainder of this disclosure. It should be understood, however, that the elongate medical device 14 may also be or include a guidewire, an introducer, or some other elongate medical device.

The catheter 14 may include, in an embodiment, various components for performing an ablation procedure, including components for delivering ablation energy and making various measurements relevant to the delivery of the ablation energy. For example, the catheter 14 may include a force sensor 15 (see FIG. 2) and an ablation electrode 17, in an embodiment. In addition, the catheter 14 may include a handle 42, a shaft 44, and other components, which are illustrated in and will be described with respect to FIGS. 1 and 2.

Figure 2:
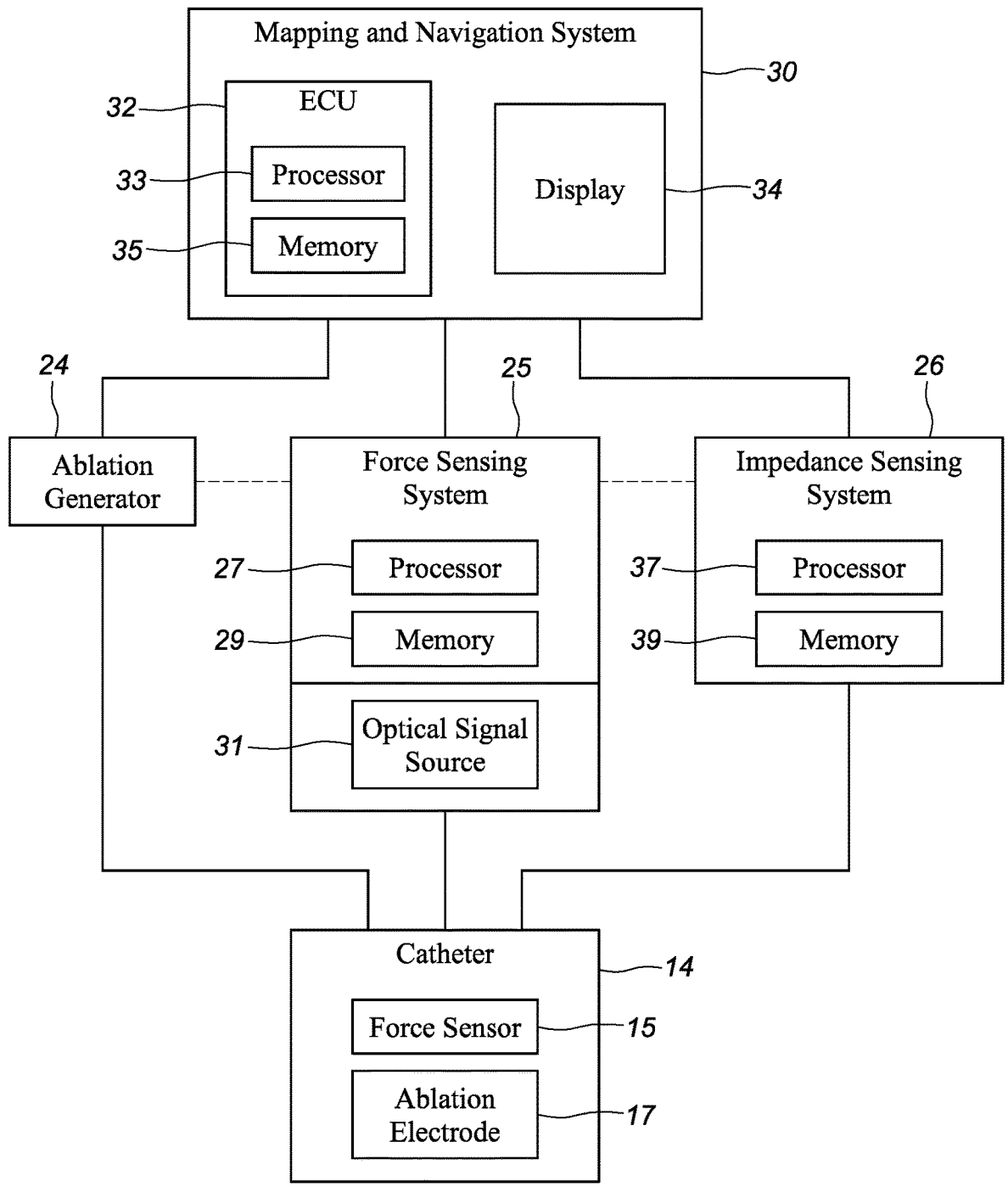
FIG. 2 is a block diagram view of an exemplary embodiment of a system for performing a medical procedure.

With continued reference to FIGS. 1 and 2, the ablation electrode 17 may be provided for the catheter 14 to deliver ablation energy to tissue 16 of a patient 19. One or more such ablation electrodes 17 may be provided. The ablation electrode 17 may be or may include a ring electrode, tip electrode, spot electrode, etc.

Figure 3:
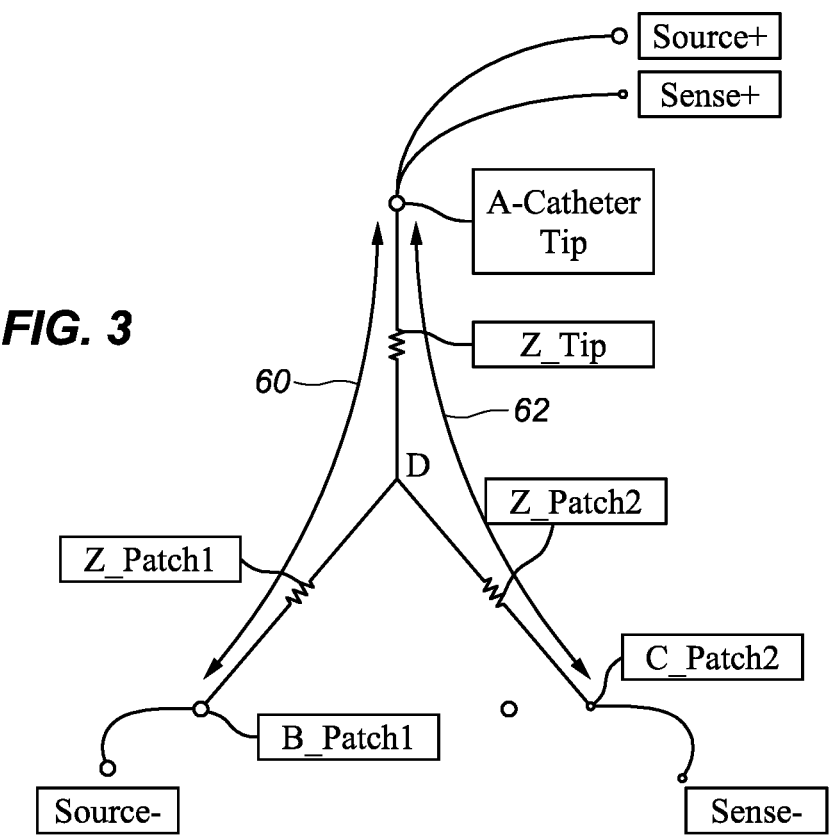
FIG. 3 is a schematic view of a portion of the system of FIG. 1, illustrating an arrangement for determining a complex impedance.
Figure 4:
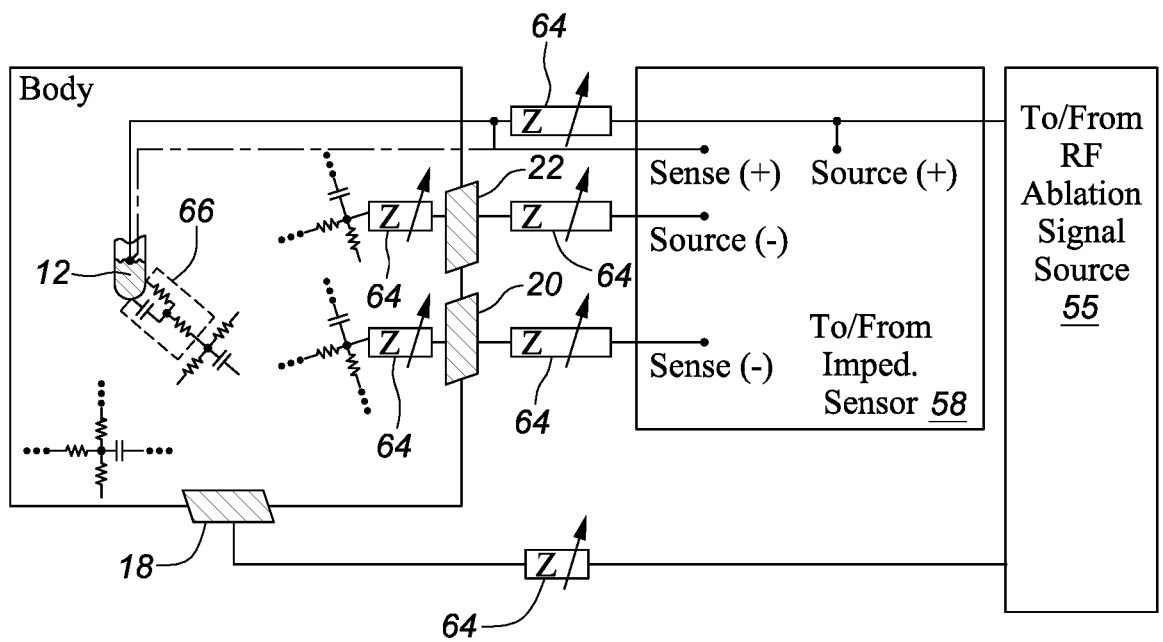
FIG. 4 is an expanded schematic and block diagram view of the arrangement of FIG. 3.

The impedance sensing system 26 (FIG. 2) may be provided for measuring tissue impedance. The impedance sensing system 26 may be, or may include, an electrode (e.g., the ablation electrode 17, a patch electrode 20, and a patch electrode 22) and an impedance sensor 58. In an embodiment in which the impedance sensing system 26 generates a signal, a current may be driven between a first electrode and a second electrode, as illustrated in FIGS. 2-4 and described below, to determine an impedance of the tissue 16, which may be a complex impedance. The impedance of the tissue 16 can be measured, for example, using a patch electrode at a location on the body 19 such as patch electrodes 18, 20, and 22. The impedance of the tissue 16 can also be measured using one or more electrodes (e.g., multi-electrode impedance or dipole) similar to the description in U.S. Patent Application Publication No. 2014/0364715, the entirety of which is incorporated herein by reference as though fully set for herein.

Continuing to refer to FIG. 2, the force sensor 15 may be provided for a measurement of contact force between the catheter 14 and tissue 16. For example, the force sensor 15 may be configured to generate an output from which a contact force magnitude and/or force vector may be measured. The contact force may be respective of contact between a portion of the catheter 14 (e.g., the ablation electrode 17) and tissue 16, in an embodiment. The force sensor 15 may comprise an optical sensor, in an embodiment. For example, the force sensor 15 may comprise one or more optical fibers having one or more interferometry-based elements, such as fiber bragg gratings (FBGs), in an embodiment. Additionally, or alternatively, the force sensor 15 may comprise one or more optical fibers terminating into or otherwise projecting light into or onto a reflective surface or surfaces in the distal end 48 (FIG. 1) of the catheter 14, such that the amount of light reflected by the reflective surfaces changes as the amount and direction of force between the catheter 14 and tissue 16 changes. In an exemplary embodiment, the catheter 14 may include three optical fibers, each including one or more respective interferometry elements and/or reflective elements. In other embodiments, one or more different types of force sensors can be used to determine contact force and the total force between the catheter tip and tissue 16. For example, force sensor types could include ultrasound, magnetic, impedance, strain gauge, piezoelectric, or other sensors known in the art for detecting force can be used.

The ablation generator 24 may be coupled with the catheter 14 (e.g., electrically coupled with the ablation electrode 17) and configured to provide ablation energy to the catheter 14 (e.g., to the ablation electrode 17). For example, the ablation generator 24 may provide an electrical signal at about 450 MHz, in an embodiment. The ablation generator 24 may be further configured to measure an impedance of tissue 16, in an embodiment.

The force sensing system 25 (FIGS. 1 and 2) may be coupled with the force sensor 15 (FIG. 2) for determining a contact force between the catheter 14 and tissue 16. The force sensing system 25 may include a processor 27, a memory 29, and an optical signal source 31, in an embodiment. The optical signal source 31 may be coupled with one or more optical fibers in the catheter 14 and configured to provide an optical signal through the optical fibers. The force sensing system 25 may be further configured to receive the reflected optical signal and calculate a contact force based on the reflected optical signal. In an embodiment, the optical signal source 31 may be configured to generate and transmit optical signals for three optical fibers in the catheter, and the force sensing system 25 may be configured to receive three reflected optical signals and calculate a contact force vector (e.g., magnitude and direction) between the catheter 14 and tissue 16.

The force sensing system 25 and force sensor 15 may include technology similar to or the same as that used in the TactiCath™ Quartz™ Ablation Catheter system, commercially available from St. Jude Medical, Inc. of St. Paul Minnesota. Additionally, or alternatively, the force sensing system 25 and force sensor 15 may include force sensing sensors, systems, and techniques illustrated and/or described in one or more of U.S. Patent Application Publication Nos. 2007/0060847; 2008/0009750; and 2011/0270046, each of which is hereby incorporated by reference in its entirety as though fully set forth herein.

The force sensing system 25 may be configured to calculate a metric that estimates a lesion size index, in an embodiment. Several embodiments of such metrics are described in detail in U.S. Patent Application Publication No. 2007/0060847, referenced above. Brief descriptions of exemplary embodiments of such metrics are also set forth below.

A first lesion size estimation metric that may be calculated by the force sensing system is a lesion size index (LSI). An LSI calculation may be performed according to the general form of equation (1) below:

$$LSI(F, I, t) = k_1\left(f_2\left(1 - e^{-\frac{F}{f_1}}\right) + f_0\right) * i_2\left(1 - e^{-\left(\frac{I}{i_1}\right)^2}\right) * \left((1-k_0) + k_0 \frac{1 - e^{\frac{-t}{\tau}}}{1 - e^{\frac{-T}{\tau}}}\right) \quad (1)$$

wherein F is force in grams, I is current in milliamps, t is a time in seconds, $f_0$, $f_1$, and $f_2$ are force parameter coefficients, $i_1$ and $i_2$ are electrical current coefficients, $k_0$ is a diffusive heating coefficient, $k_1$ is a rescaling coefficient, and $\tau$ is a characteristic time value. The output LSI is in millimeters.

The LSI model reflected in Eq. (1) comprises a joule heating component $1-k_0$ that is independent of time and a diffusive heating component $$k_0 \frac{1 - e^{\frac{-t}{\tau}}}{1 - e^{\frac{-T}{\tau}}}$$

that is a function of time. The joule heating and diffusive heating components are multiplied by the lesion depth estimated for an ablation lasting a time period of T, with the averaged force F and electrical current I over the time period T. Data analyzed in the development of this LSI formulation was generated for a time period T of 60 seconds. It is noted that the baseline time of 60 seconds was a result of the availability of lesion data that was based on ablation times of 60 seconds. Data from ablations of different durations (e.g., 30 sec. or 45 sec.) can also be used in a form similar to Eq. (1) by substitution of the appropriate time for the "60" found in the numerator of the diffusive heating component.

Numerous varieties of LSI exist. For example, lesion width index (LWI) and lesion depth index (LDI) are two, each of which may be used to estimate lesion size. LWI and LDI may be calculated according to an equation of the same form as LSI (i.e., Eq. (1) above), but with different coefficient values. Exemplary coefficient values, which may be determined experimentally, are given in Table (1) below.

TABLE (1)

|     | $f_2$ | $f_1$ | $f_0$ | $i_2$ | $i_1$ | $k_0$ | $k_1$ | T |
|-----|-------|-------|-------|-------|-------|-------|-------|-------|
| LDI | 4.36 | 20.67 | 2.17 | 2.57 | 630.75 | 0.578 | $\frac{1.22}{\sqrt{2}}$ | 38.57 |
| LWI | 3.74 | 18.2 | 1.99 | 3.29 | 525.85 | 0.481 | 1.1 | 29.23 |

The impedance sensing system 26 may be provided for determining an impedance of tissue 16, such as a complex impedance. As shown in FIGS. 1 and 2, the impedance sensing system 26 may include a processor 37, a memory 39, and a tissue sensing circuit that can include a signal generator 61 and a sensor 58 in an embodiment. The impedance sensing system 26 may be electrically coupled with the catheter 14 (e.g., with the ablation electrode 17 and/or one or more other electrodes on the catheter 14), may drive a signal from the signal generator 61 to the ablation electrode 17 and/or other electrodes (e.g., patch electrodes 18, 20, and 22), and may analyze the signal to determine one or more components of a complex impedance (e.g., a magnitude, phase angle, resistance, and/or reactance) of the tissue 16. The functionality of the impedance sensing system 26 is described in further detail below with reference to FIGS. 1-4.

Referring still to FIGS. 1 and 2, the mapping and navigation system 30 may be provided to enable a clinician to visualize tissue 16 and to navigate the catheter 14 to and around tissue 16 targeted for diagnosis or therapy, among other functions. Accordingly, the mapping and navigation system 30 may be provided with a variety of functions, including the generation and display of models of tissue, generation and display of electrophysiological (EP) maps of tissue 16, tracking of the catheter, and superimposition of the catheter 14 on a display 34 of one or more maps or models to enable a clinician to view the location of the catheter 14 relative to tissue 16, among other functions. The mapping and navigation system 30 may comprise an ECU 32 and a display 34, with the ECU 32 including a processor 33 and a memory 35, for carrying out the functions described herein and/or other functions.

The mapping and navigation system 30 may be, or may include, an EnSite™ Velocity™ system, commercially available from St. Jude Medical, Inc. and as generally shown with reference to commonly assigned U.S. Pat. No. 7,263,397, the entire disclosure of which is incorporated herein by reference. The mapping and navigation system 30 may additionally or alternatively include the Biosense Webster CARTO™ system, the Boston Scientific RHYTHMIA™ system, commonly available fluoroscopy systems, or a magnetic-field-based system such as one based on the Medi-Guide™ technology commercially available from St. Jude Medical, Inc.

In an embodiment, the mapping and navigation system 30, the ablation generator 24, the force sensing system 25, and the impedance sensing system 26 may be in communication with each other in various configurations for the exchange of data, the routing of electrical signals, and other functions. In an embodiment, the exchange of data and routing of signals may contribute to an ablation procedure with the catheter 14 in which one or more of force data derived from measurements with the force sensor 15, impedance data derived from measurements with the impedance sensing system 26, and energy delivered with the ablation electrode 17 are used to characterize tissue morphology and/or to calculate a predicted or estimated lesion size. Before turning to tissue morphology characterization and lesion size estimation in greater detail, the operation of the impedance sensing system 26 and ablation generator 24 will be described in greater detail, along with additional features of the catheter 14.

Ablation and Impedance Sensing Aspects of the System

FIG. 1 is a diagrammatic view of a system for performing an ablation procedure. The system includes numerous components found also in the system of FIG. 2. In particular, the system of FIG. 1 includes ablation and impedance-sensing components also found in the system of FIG. 2, and thus the discussion of such aspects with respect to FIG. 1 should be considered to apply to the system of FIG. 2, as well.

An embodiment similar to the system of FIGS. 1, 3, and 4, and its use to determine, e.g., an ECI value, is described in detail in U.S. Pat. No. 8,403,925, which is incorporated by reference herein in its entirety as though fully set forth herein. Additional information about ECI and lesion monitoring is described in U.S. Patent Application Publication Nos. 2011/0144524, 2011/0264000, and 2013/0226169, each of which is hereby incorporated by reference as though fully set forth herein. A brief description of the system and its use for determining a complex impedance and ECI is provided below.

The system 10 may be used to determine, among other things, an impedance, such as a complex impedance, of the tissue 16 of a patient's body, as well as one or more metrics based on that impedance, such as a degree of electrical coupling between an electrode on a catheter 14 and the tissue 16. In the illustrated embodiment, the tissue comprises heart or cardiac tissue 16. It should be understood, however, that the system 10 may be used to evaluate coupling between electrodes and a variety of different types of body tissues.

In addition to the catheter 14, the system 10 may include patch electrodes 18, 20, and 22, the ablation generator 24, an impedance sensing system 26, an electrophysiology (EP) monitor 28, and the mapping and navigation system 30.

The catheter 14 may be connected to a fluid source 36 for delivering a biocompatible fluid such as saline through a pump 38 (which may comprise, for example, a fixed rate roller pump or variable volume syringe pump with a gravity feed supply from the fluid source, as shown) for irrigation. The catheter 14 may also be electrically connected to the ablation generator 24 for delivery of RF energy. The catheter 14 may include a cable connector or interface 40, a handle 42, a shaft 44 having a proximal end 46 and a distal end 48 (as used herein, "proximal" refers to a direction toward the end of the catheter 14 near the clinician, and "distal" refers to a direction away from the clinician and (generally) inside the body of a patient), and one or more electrodes. The catheter 14 may also include other conventional components not illustrated herein such as a temperature sensor, additional electrodes, and corresponding conductors or leads.

The connector 40 may provide mechanical, fluid, and electrical connection(s) for cables 54 and 56 extending, for example, from the pump 38 and the ablation generator 24. The connector 40 may be conventional in the art and may be disposed at the proximal end of the catheter handle 42.

The handle 42 may provide a location for the clinician to hold the catheter and may further provide means for steering or guiding the shaft 44 within the body 19. For example, the handle 42 may include means to change the length of a guidewire extending through the catheter 14 to the distal end 48 of the shaft 44 to steer the shaft 44. The handle 42 may also be conventional in the art. In an alternate exemplary embodiment, the catheter may be robotically driven or controlled. Accordingly, rather than a clinician manipulating a handle to steer or guide a catheter, and the shaft thereof, in particular, a robot may be used to manipulate the catheter.

The shaft 44 may be an elongate, tubular, flexible member configured for movement within the body 19. The shaft 44 may support the electrodes 50 and 52, associated conductors, and possibly additional electronics used for signal processing or conditioning. For example, the shaft 44 may further include the force sensor. The shaft may also permit transport, delivery, and/or removal of fluids (including irrigation fluids and bodily fluids), medicines, and/or surgical tools or instruments. The shaft 44 may be made from conventional materials such as polyurethane and may define one or more lumens configured to house and/or transport electrical conductors, fluids, or surgical tools.

The electrodes 50 and 52 may be provided for a variety of diagnostic and therapeutic purposes including, for example, electrophysiological studies, catheter identification and location, pacing, cardiac mapping, and ablation. The catheter 14 may include an ablation tip electrode 17 at the distal end 48 of the shaft 44, in an embodiment. It should be understood, however, that the number, shape, orientation, and purpose of the electrodes (e.g., 17, 50, 52) may vary.

The patch electrodes 18, 20, and 22 may provide RF or navigational signal injection paths and/or are used to sense electrical potentials. The patch electrodes 18, 20, and 22 may be made from flexible, electrically-conductive material and may be configured for affixation to the body such that the patch electrodes are in electrical contact with the patient's skin. Another electrode may function as an RF indifferent/dispersive return for the RF ablation signal. The electrodes may function as returns for the RF ablation signal source 55 and/or an excitation signal generated by the impedance sensing system 26 as described in greater detail below.

The ablation generator 24 may generate, deliver, and control RF energy for output by the catheter 14 (e.g., through one or more of the electrodes on the catheter). The generator 24 may include an RF ablation signal source configured to generate an ablation signal that is output across a pair of source connectors: a positive polarity connector SOURCE (+) which may connect to the tip electrode; and a negative polarity connector SOURCE (−) which may be electrically connected by conductors or lead wires to one of the patch electrodes (sec, e.g., FIG. 3). It should be understood that the term connectors as used herein does not imply a particular type of physical interface mechanism, but is rather broadly contemplated to represent one or more electrical nodes. The source 55 may be configured to generate a signal at a predetermined frequency in accordance with one or more user specified parameters (e.g., power, time, etc.) and under the control of various feedback sensing and control circuitry. The source 55 may generate a signal, for example, with a frequency of about 450 kHz or greater.

The generator 24 may also monitor various parameters associated with the ablation procedure including impedance, the temperature at the tip of the catheter, and ablation energy; and the generator may provide feedback to the clinician regarding these parameters. The impedance measurement output by the generator may reflect the entire impedance between the tip electrode and the indifferent patch electrode. In an exemplary embodiment, the ablation generator 24 may generate a higher frequency current for the purposes of RF ablation, and a second lower frequency current for the purpose of measuring impedance.

The impedance sensing system 26 may provide an apparatus, such as a tissue sensing signal source 61, for generating an excitation signal used in impedance measurements and means, such as a complex impedance sensor 58, for resolving the detected impedance into its component parts. The signal source 61 may be configured to generate an excitation signal across source connectors SOURCE (+) and SOURCE (−) (see FIG. 3). The source 61 may output a signal having a frequency within a range from about 1 kHz to over 500 kHz, more preferably within a range of about 2 kHz to 200 kHz, and even more preferably about 20 kHz. In one embodiment, the excitation signal may be a constant current signal, preferably in the range of between 20-200 µA, and more preferably about 100 µA. As discussed below, the constant current AC excitation signal generated by the source 61 may be configured to develop a corresponding AC response voltage signal that is dependent on the complex impedance of the tissue and is sensed by the complex impedance sensor 58. The complex impedance is resolved into its component parts (i.e., the resistance (R) and reactance (X) or the impedance magnitude (|Z|) and phase angle (∠Z or Ø)). The impedance sensor 58 may include conventional filters (e.g., bandpass filters) to block frequencies that are not of interest, but permit appropriate frequencies, such as the excitation frequency, to pass, as well as conventional signal processing software used to obtain the component parts of the measured complex impedance.

It should be understood that several variations are possible. For example, the excitation signal may be an AC voltage signal where the response signal comprises an AC current signal. Nonetheless, a constant current excitation signal is preferred as being more practical. Although in some situations there can be advantages to having an excitation signal frequency at or near the frequency of the RF ablation signal, it should be appreciated that the excitation signal frequency is preferably outside of the frequency range of the RF ablation signal, which allows the complex impedance sensor to more readily distinguish the two signals, and facilitates filtering and subsequent processing of the AC response voltage signal. Alternatively, the system can cycle each signal (RF ablation and excitation) on and off in alternating periods so they do not overlap in time. The excitation signal frequency is also preferably outside the frequency range of conventionally expected electrogram (EGM) signals in the frequency range of 0.05 Hz-1 kHz. Thus, in summary, the excitation signal preferably has a frequency that is preferably above the typical EGM signal frequencies and below the typical RF ablation signal frequencies.

The impedance sensing system may also be connected, for a purpose described below, across a pair of sense connectors: a positive polarity connector SENSE (+) which may connect to the tip electrode 17; and a negative polarity connector SENSE (−) which may be electrically connected to one of the patch electrodes 18, 20, and 22 (see FIGS. 1 and 3; note, however, that the connector SENSE (−) should be connected to a different electrode of the patch electrodes 18, 20, and 22 relative to the connector SOURCE (−) as discussed below). It should again be understood that the term connectors as used herein does not imply a particular type of physical interface mechanism, but is rather broadly contemplated to represent one or more electrical nodes.

Referring now to FIG. 3, connectors SOURCE (+), SOURCE (−), SENSE (+), and SENSE (−) form a three terminal arrangement permitting measurement of the complex impedance at the interface of the tip electrode and the tissue. Complex impedance can be expressed in rectangular coordinates as set forth in equation (2) below:

$$Z = R + jX \quad (2)$$

where R is the resistance component (expressed in ohms); and X is a reactance component (also expressed in ohms).

Complex impedance can also be expressed polar coordinates as set forth in equation (3) below:

$$Z = r \cdot e^{j\theta} |Z| \cdot e^{j\angle Z} \quad (3)$$

where |Z| is the magnitude of the complex impedance (expressed in ohms) and ∠Z=θ is the phase angle expressed in radians. Alternatively, the phase angle may be expressed in terms of degrees where $$\phi = \left(\frac{180}{\pi}\right)\theta.$$

Throughout the remainder of this specification, phase angle will be preferably referenced in terms of degrees.

Three terminals are illustrated in FIG. 3, and those terminals comprise: (1) a first terminal designated "A-Catheter Tip," which is the tip electrode 17; (2) a second terminal designated "B_Patch 1," which may be the source return patch electrode 22; and (3) a third terminal designated "C_Patch 2," which may be the sense return patch electrode 20. In addition to the ablation (power) signal generated by the signal source 55 of the ablation generator 24, the excitation signals 60 and 62 generated by the source 61 in the impedance sensing system 26 may also be applied across the source connectors (SOURCE (+), SOURCE (−)) for the purpose of inducing a response signal with respect to the load that can be measured and which depends on the complex impedance. As described above, in one embodiment, a 20 kHz, 100 µA AC constant current signal 60 is sourced along a path, as illustrated, from one connector (SOURCE (+), starting at node A) through the common node (node D) to a return patch electrode (SOURCE (−), node B). The complex impedance sensor 58 may be coupled to the sense connectors (SENSE (+), SENSE (−)), and is configured to determine the impedance across a path 62. For the constant current excitation signal of a linear circuit, the impedance will be proportional to the observed voltage developed across SENSE (+)/SENSE (−), in accordance with Ohm's Law: Z=V/I. Because voltage sensing is nearly ideal, the current flows through the path 60 only, so the current through the path 62 (node D to node C) due to the excitation signal is effectively zero. Accordingly, when measuring the voltage along the path 62, the only voltage observed will be where the two paths intersect (i.e., from node A to node D). Depending on the degree of separation of the two patch electrodes (i.e., those forming nodes B and C), an increasing focus will be placed on the tissue volume nearest the tip electrode 17. If the patch electrodes are physically close to each other, the circuit pathways between the catheter tip electrode 17 and the patch electrodes may overlap significantly and impedance measured at the common node (i.e., node D) may reflect impedances not only at the interface of the catheter tip electrode 17 and the tissue 16, but also other impedances between the tissue 16 and the surface of the body 19. As the patch electrodes are moved further apart, the amount of overlap in the circuit paths may decrease, and impedance measured at the common node may be only at or near the tip electrode 17 of the catheter 14.

Referring now to FIG. 4, the concept illustrated in FIG. 3 is extended. FIG. 4 is a simplified schematic and block diagram of the three-terminal measurement arrangement illustrated in FIG. 3. For clarity, it should be pointed out that the SOURCE (+) and SENSE (+) lines may be joined in the catheter connector or the handle (as in solid line) or may remain separate all the way to the tip electrode 17 (the SENSE (+) line being shown in phantom line from the handle to the tip electrode 17). FIG. 4 shows, in particular, several sources of complex impedance variations, shown generally as blocks 64, that are considered "noise" because such variations do not reflect the physiologic changes in the tissue or electrical coupling whose complex impedance is being measured. For reference, the tissue for which complex impedance is being measured is that near and around the tip electrode 17 and is enclosed generally by a phantom-line box 66 (and the tissue 16 is shown schematically, in simplified form, as a resistor/capacitor combination). One object is to provide a measurement arrangement that is robust or immune to variations that are not due to changes in or around the box 66. For example, the variable complex impedance boxes 64 that are shown in series with the various cable connections (e.g., in the SOURCE (+) connection, in the SOURCE (−) and SENSE (−) connections, etc.) may involve resistive/inductive variations due to cable length changes, cable coiling and the like. The variable complex impedance boxes 64 that are near the patch electrodes 18, 20, and 22 may be more resistive/capacitive in nature, and may be due to body perspiration and the like over the course of a study. As will be seen, the various arrangements of the system 10 are relatively immune to the variations in the blocks 64, exhibiting a high signal-to-noise (S/N) ratio as to the complex impedance measurement for the block 66.

Although the SOURCE (−) and SENSE (−) returns are illustrated in FIG. 4 as patch electrodes 18, 20, and 22, it should be understood that other configurations are possible. In particular, the indifferent/dispersive return electrode 18 may be used as a return as well as another electrode 50, 52, on the catheter 14, such as the ring electrode 50, as described in commonly assigned U.S. Patent Application Publication No. 2009/0171345, the entire disclosure of which is incorporated herein by reference as though fully set forth herein.

The EP monitor 28 (FIG. 1) may be provided to display electrophysiology data including, for example, an electrogram. The monitor 28 may be conventional in the art and may comprise an LCD or CRT monitor or another conventional monitor. The monitor 28 may receive inputs from the ablation generator 24 as well as other conventional EP lab components not shown in the illustrated embodiment.

The ECU 32 may be configured to acquire values of a complex impedance (e.g., a resistance and reactance and/or magnitude and phase angle) between the catheter tip electrode 17 and the tissue 16 and to calculate a metric responsive to the values that is indicative of a degree of coupling between the electrode and the tissue. For example, the ECU 32 may be configured to calculate an electrical coupling index (ECI).

The ECU 32 may be configured to acquire values for two component parts of the complex impedance from signals generated by the sensor of the impedance sensing system 26 (i.e., the resistance (R) and reactance (X) or the impedance magnitude (|Z|) and phase angle (Ø) or any combination of the foregoing or derivatives or functional equivalents thereof). The ECU 32 may be further configured to combine values for the two components into a single ECI value that provides an improved measure of the degree of coupling between the electrode and the tissue and, in particular, the degree of electrical coupling between the electrode 17 and the tissue 16.

In an embodiment in which the resistance and reactance components of complex impedance are used, an ECI value may be determined according to equation (4) below:

$$ECI = a*\overline{R} + b*\overline{X} + c \tag{4}$$

Where $\overline{R}$ and $\overline{X}$ are the mean values of a resistance and reactance, respectively, and a, b, and c are experimentally-determined coefficients that account for, e.g., the specific equipment used for measurement. As used herein, the "mean value" for the resistance or reactance (denoted by $\overline{R}$ and $\overline{X}$) may refer to the average of N samples of a discrete time signal $x_i$ or a low-pass filtered value of a continuous $x(t)$ or discrete $x(t_i)$ time signal.

In a specific embodiment, using a four (4) millimeter (mm) irrigated tip catheter, an ECI value may be determined according to equation (5) below:

$$ECI = \overline{R} - 5.1*\overline{X} \tag{5}$$

It should be understood that other values associated with the impedance components, such as a standard deviation of a component or peak-to-peak magnitude of a component which reflect variation of impedance with cardiac motion or ventilation, can also serve as useful factors in embodiments of an ECI calculation. Further, although the above equations focus on the rectangular coordinates of resistance (R) and reactance (X), it should be understood that the ECI value could also be based on values associated with the polar coordinates impedance magnitude (|Z|) and phase angle (Ø) or indeed any combination of the foregoing components of the complex impedance and derivatives or functional equivalents thereof. Finally, it should be understood that coefficients, offsets, and values within the equation for the ECI value may vary depending on, among other things, the specific catheter used, the patient, the equipment, the desired level of predictability, the species being treated, and disease states.

As noted above, an ECI value may be used, in conjunction with other factors, to characterize tissue morphology and/or to estimate or predict lesion size. In addition to an ECI value, additional metrics calculated from a complex impedance may find use in tissue morphology characterization and/or lesion size prediction or estimation. For example, an electrical coupling index rate (ECIR) or the rate of change of the ECIR.

ECIR may generally include a change in ECI over time and over distance. In an embodiment, ECIR may be calculated by dividing the change in ECI by a distance (i.e., a change in position of the electrode) over a period of time. More specifically, in an embodiment, ECIR may be calculated according to equation (6) below:

$$ECIR := \frac{dECI}{ds} = \frac{dECI/dt}{ds/dt} \tag{6}$$

The rate of change of ECIR may be calculated according to equation (7) or equation (8) below:

$$dECIR = \frac{d}{dt}\left(\frac{dECI}{ds}\right) \quad (7)$$

$$dECIR = \frac{d/dt : (dECI/ds)}{ds/dt} = \frac{d^2ECI}{ds^2} \quad (8)$$

Tissue Characterization and Lesion Size Estimation

An impedance, or an impedance-based metric, may be used in conjunction with contact force to characterize tissue and/or to provide improved lesion size estimation or prediction. More specifically, in an embodiment, the ratio of an impedance or an impedance-based metric to contact force may be used to characterize tissue and/or to provide improved lesion size estimation.

Referring again to FIGS. 1 and 2, the system 10 may be configured to utilize data from the impedance sensing system 26, the force sensing system 25, the ablation generator 24 and/or other source(s) to characterize tissue morphology and/or to estimate lesion size. One or more of the ECU 32 of the mapping and navigation system 30, the force sensing system 25, and the impedance sensing system 26 may be configured to perform tissue morphology characterization and/or lesion size estimation based on the data generated within the system. That is, one or more of the memories may store instructions that, when executed by the associated processor, cause the ECU 32, force sensing system 25, or impedance sensing system 26 to perform one or more steps, processes, or methods described herein for characterizing tissue morphology and/or estimating lesion size.

In embodiments, the ECU 32 of the mapping and navigation system 30, the force sensing system 25, and the impedance sensing system 26 may be implemented as three separate computing systems, as schematically represented in FIG. 2. Alternatively, the ECU 32 of the mapping and navigation system 30, the force sensing system 25, and the impedance sensing system 26, or the functionality thereof, may be implemented or distributed in a single computing apparatus, two computing apparatus, or any other number of computing apparatus. Accordingly, although particular functionality is described with respect to particular systems in this disclosure, it should be understood that such description is exemplary in nature only.

In an embodiment, the various systems and devices of the system 10 may be in communication with and/or electrically coupled with each other for the transmission of data and electrical signals. For example, the mapping and navigation system 30 may be in communication with the ablation generator 24 for the mapping and navigation system 30 to control the ablation generator 24 (e.g., to control the provision of ablation energy), to receive an impedance measured by the ablation generator 24, etc. The ablation generator 24 may additionally or alternatively be in communication with and/or electrically coupled with the force sensing system 25 and/or the impedance sensing system 26 (an electrical and communicative coupling between the ablation generator 24 and the force sensing system 25 is indicated by a dashed line in FIG. 2) for the routing of ablation energy from the ablation generator 24 to the catheter 14, as well as for the provision of an impedance measured by the ablation generator 24 to the force sensing system 25 and/or the impedance sensing system 26.

The force sensing system 25 may be in communication with the mapping and navigation system 30 for the mapping and navigation system 30 to control the operation of the force sensing system 25 and/or for the force sensing system 25 to provide measurements and calculations made at or by the force sensing system 25 to the mapping and navigation system 30. For example, the force sensing system 25 may be configured to provide a force vector, or a metric based on the force vector (e.g., an LSI, LWI, LDI, etc.), to the mapping and navigation system 30. Based in part on such data, the ECU 32 of the mapping and navigation system 30 may characterize tissue morphology and/or estimate a lesion size.

The impedance sensing system 26 may be in communication with the mapping and navigation system 30 for the mapping and navigation system 30 to control the operation of the impedance sensing system 26 and/or for the impedance sensing system 26 to provide measurements and calculations made at or by the impedance sensing system 26 to the mapping and navigation system 30. For example, the impedance sensing system 26 may be configured to provide a complex impedance, one or more components of a complex impedance, and/or a metric based on the complex impedance or components of the complex impedance (e.g., an ECI value, ECIR value, rate of change of ECIR, etc.) to the mapping and navigation system 30. Based in part on such data, the ECU 32 of the mapping and navigation system 30 may characterize tissue morphology and/or estimate a lesion size.

In current clinical practice, assessment of ablation catheter tip contact with the cardiac tissue is evaluated using either contact force or impedance measurements. Although these two measurements are perceived to provide similar information with respect to electrode contact with the tissue, they provide fundamentally different but potentially complimentary information. Impedance measured between the catheter tip and the tissue is influenced by a number of factors such as temperature, anatomy/pathology/morphology of the tissue being contacted, as well as the degrees of electrode/tissue contact. In the intracardiac environment, differences in anatomy/pathology include, for example, smooth vs. trabeculated (pectinated) tissue; healthy myocardium vs. scar tissue; and healthy vs. ablated myocardium. The relationship between force and impedance differs depending on the characteristics of the underlying tissue.

Figure 5:
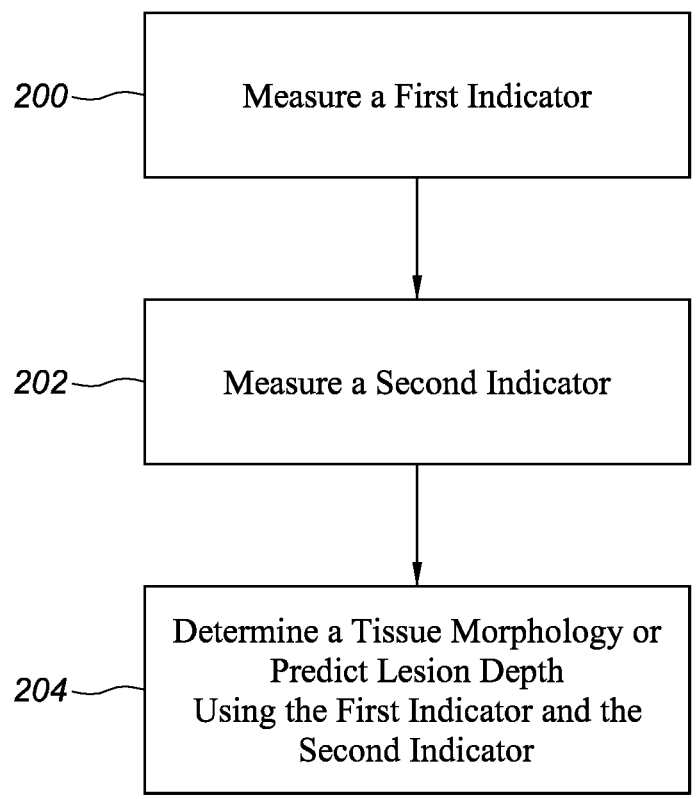
FIG. 5 is a high-level flow chart of exemplary steps for using a first indicator and a second indicator when, for example, determining a tissue morphology/characterization or predicting a lesion size.

FIG. 5 is a high-level flow chart of exemplary steps for using a first indicator and a second indicator when determining, for example, a tissue morphology/characterization or predicting a lesion size (e.g., depth, width, depth at maximum diameter, volume, cross-sectional area). When determining a tissue morphology, the first indicator may be, for example, a measure of contact force (e.g., the magnitude of a contact force between a catheter tip and tissue); and the second indicator may be, for example, a measure of a resistance between a catheter tip and tissue, a measure of reactance between a catheter tip and tissue, an ECI value between a catheter tip and tissue, or an RF generator impedance. When predicting a lesion depth, the first indicator may be, for example, an LSI value; and the second indicator may represent, for example, a tissue characterization. The steps can include measuring (at box 200) the first indicator, measuring (at box 202) the second indicator, and determining a tissue morphology or predicting a lesion depth (at box 204) using both the first indicator and the second indicator.

Figure 6:
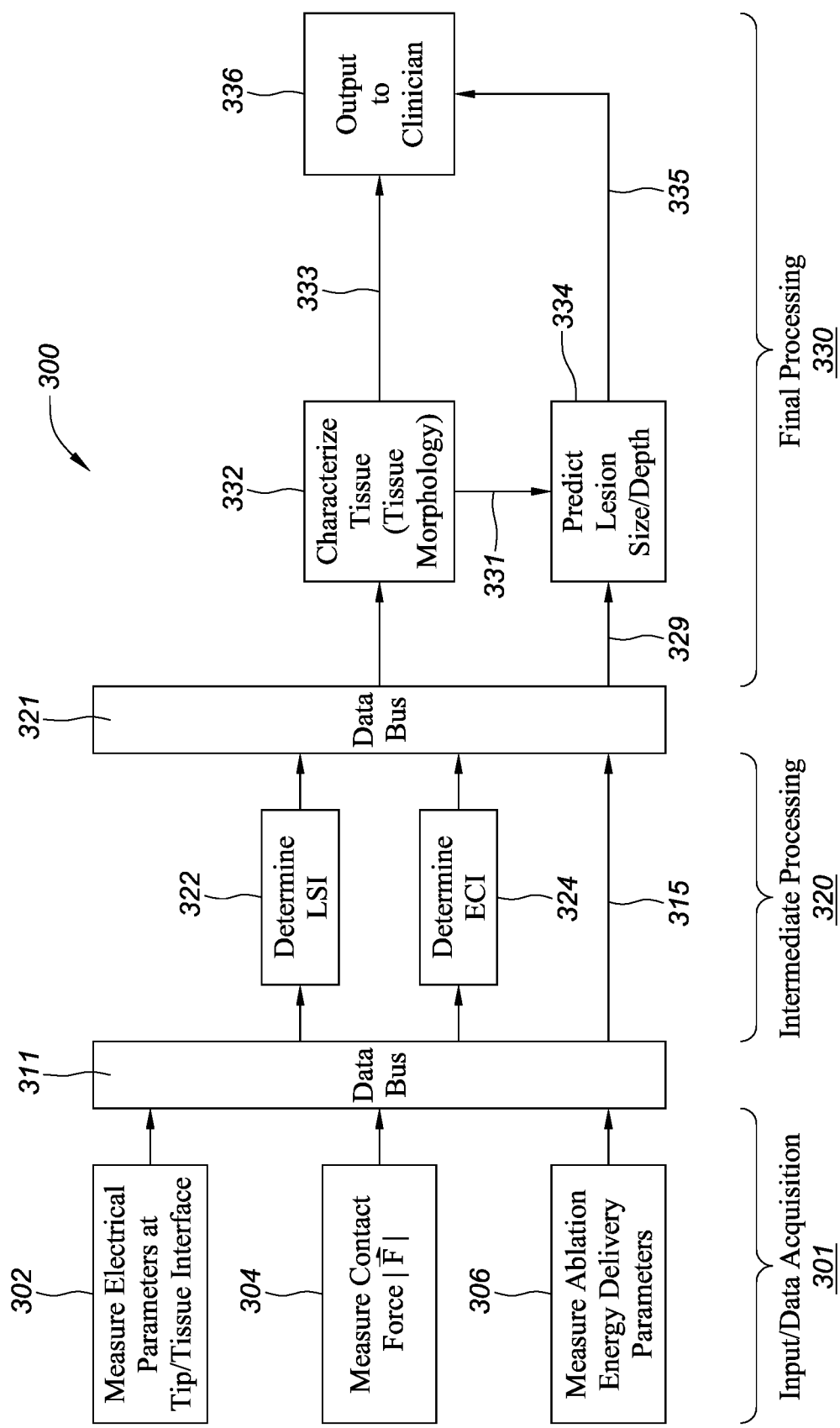
FIG. 6 is a high-level flow chart of one variation of how a variety of inputs may be collected and used in a system configured to, ultimately, present useful information to a clinician or other user.

FIG. 6 depicts a high-level flow chart 300 of one variation of how a variety of inputs may be collected and used in a system configured to, ultimately, present useful information (such as tissue morphology and/or predicted lesion depth) to a clinician or other system user. The system may comprise various components for collecting, storing, processing, and presenting useful results to clinicians. For example, the underlying system may include hardware for receiving data; hard drives or other data storage devices for volatile and nonvolatile storage of information; and one or more central processing units or other computing devices (e.g., PLCs or ASICs) to control the hardware, run programs and other routines, move data between system components, make calculations, and to cause the display or other presentation of results to users such as physicians or clinicians. Sharing of data may occur through, for example, data buses depicted schematically in FIG. 6 as elongated boxes 311 and 321. The particular configuration of a system to carry out the operations represented by the flow chart of FIG. 6 described further below could vary significantly from what is described herein.

The overall process represented by the flow chart 300 of FIG. 6 may be thought of as comprising three primary stages to collect inputs, calculate values, and generate output for a clinician: (a) an input/data acquisition stage 301; (b) an intermediate processing stage 320; and a final processing stage 330, which, in the depicted example, includes outputting some type of result or results to a clinician. From a high level, the process involves gathering various inputs during the input/data acquisition stage 301, determining one or more intermediate values (such as an LSI value (see box 322) and/or an ECI value (see box 324)) during the intermediate processing stage 320. During the final processing stage 330, the intermediate values are used in combination with one or more additional pieces of information gathered during the input/data acquisition stage 301 to, for example, characterize the tissue and/or to predict the depth of a lesion. In one embodiment, the characterization of the tissue is, itself, an intermediate value that may be used during the lesion prediction process. Finally, also during the final processing stage 330, clinically-relevant information is presented to a clinician (e.g., by presenting various numbers, colors, and/or patterns on a computer screen as described further below).

In one embodiment, a tissue characterization (or tissue morphology) "value" is determined in box 332 by taking a ratio of an ECI value determined in box 324 (e.g., using the data gathered during the input/data acquisition stage 301) to a measure of contact force (e.g., also gathered during the input/data acquisition stage 301 and conceptually depicted in FIG. 6 as then being passed through data bus 311, connector link 315, and data bus 321 to box 332). The tissue characterization value may subsequently be presented or output to a clinician at box 336 as represented by connector line 333 and box 336. The "value" output to the clinician may be in the form of, for example, one or more of a number, a color, a color intensity, a shading pattern, a shape, some other graphical representation, or any other indicator or indicators. The output generated at box 336 may alternatively or additionally include catheter feedback (e.g., sounds, indicator lights, vibrations, vibration patterns, or other aural, visual, or tactile feedback). The output value or values may inform the clinician of the particular type or types of tissue present (e.g., scar), or of important tissue characteristics (e.g., smooth, trabeculated, pectinated). The correlation between this determined tissue characterization value and actual tissue type is discussed below with reference to FIGS. 7C and 8C.

In another embodiment, the flow chart 300 depicted in FIG. 6 could be used to determine a value indicative of expected lesion size (e.g., depth, width, depth at maximum diameter, volume, cross-sectional area) using, for example, the LSI value determined in box 322 (conceptually depicted in FIG. 6 as being passed through the data bus 321 and along connector link 329 to box 334) and the tissue characterization value determined in box 332 (conceptually depicted in FIG. 6 as being passed along connector link 331 to box 334). In this embodiment, a determined value indicative of, for example, expected lesion depth could be output to the clinician as conceptually depicted by connector link 335 and box 336. Again, the "value" output to the clinician may be in the form described in the prior paragraph. The output value may also inform the clinician, for example, of an amount of energy delivered or that it is time to stop delivering ablation energy.

The data or other information acquired/measured in the input/data acquisition stage 301 and/or determined in the intermediate processing stage 320 or the final processing stage 330 in FIG. 6 is shared through a plurality of data paths (e.g., 315, 329, 331, 333, 335) and data buses (e.g., 311, 321), which may comprise components of an overall hardware and software system also including a processor or similar device to manage the movement of data and any required calculation or data lookup requirements. For example, one or more processors or similar devices involved in the data acquisition/collection of data input/acquisition step 301 may be connected to a first data bus 311 that, in turn, may be connected to one or more processors involved in the intermediate processing step 320. The one or more processors involved in the intermediate processing step 320 may, in turn, be connected to second data bus 321 that may, in turn, be connected to one or processors involved in the final processing step 330. Alternatively, a single processor or single set of processors may be used during all three of the stages 301, 320, 330; or a single processor or a single set of processors may be used during two of the stages, with a different processor or different set of processors used during the third stage.

Continuing to refer to FIG. 6, the input/data acquisition stage 301 may include, for example, measuring (at box 302) one or more electrical parameters (e.g., resistance and reactance) at an interface of a catheter tip 17 with the tissue 16. Data input acquisition step 301 may also include measuring (at box 304) a contact force between the catheter tip 17 and the tissue 16 and/or measuring (at box 306) ablation energy delivery parameters. The ablation energy delivery parameters can include, for example, a duration of time when energy is delivered to the tissue (energy delivery time), a duration of overall ablation time, a quantity of energy delivered to the tissue, and an RF generator impedance measured at, for example, the interface of the catheter tip 17 and the tissue 16. In addition to a data bus, or as an alternative embodiment, other suitable arrangements known in the art for making data available to a processor or set of processors can be used such as, for example, an information interchange network.

The intermediate processing step 320 can include, for example, one or more steps of determining (at box 322) an LSI value and determining (at box 324) an ECI value. The one or more processors or similar devices of the intermediate processing step 320 can be connected to a second data bus 321 where the second data bus 321 is connected to one or more processors or similar devices of the final processing step 330. As described above, the LSI value determined at box 322 may be determined using, for example, RF power, contact force, and time from the ablation energy delivery parameters at box 306. The ECI value at box 324 may be determined using, for example, the contact force from box 304 and the electrical parameters at the tip/tissue interface of box 302.

The accuracy of the LSI (as described in U.S. Patent Application Publication No. 2012/0209260A1, the entirety of which is incorporated by reference as though full set forth herein) can be improved by including, for example, either the ratio of RF generator impedance to the total contact force (between a catheter tip and tissue) or the ratio of ECI to total contact force. The ratio of RF generator impedance to contact force and the ratio of ECI to total contact force are larger for trabeculated cardiac tissue compared to smooth cardiac tissue.

Referring to FIGS. 7A-7D, the relationship between force and, respectively, resistance, reactance, ECI, and RF generator impedance at various locations of a swine heart show readily apparent differences between smooth (right atrium (RA) septum, posterior RA, posterior LA, and mitral annulus) and pectinated (lateral RA and RAA) tissue. The data represented in FIGS. 7A-7D was generated during intracardiac mapping in swine.

Figure 7A:
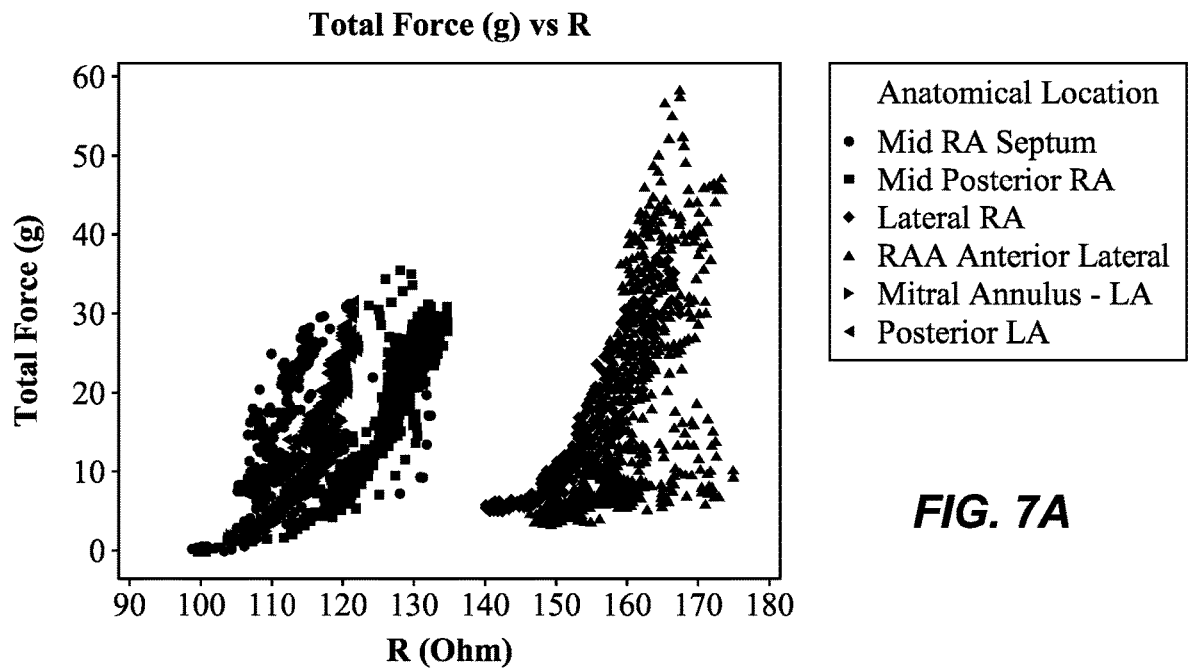
FIGS. 7A-7D are scatter plots illustrating the relationship between total contact force and, respectively, resistance, reactance, ECI, and generator impedance.

FIG. 7A shows the relationship between total force and resistance. Intracardiac data collected from healthy swine using an RF ablation generator (e.g. a VeriSense™ RF ablation generator) in combination with contact force measurements provided by a TactiCath™ Quartz™ catheter confirms that simultaneous measurements of both contact force and impedance between the catheter tip and the tissue can provide information about the underlying tissue substrate. FIG. 7A illustrates the difference in force vs. resistance (R) data pairs when the catheter tip is in contact with different anatomical areas of the heart (mid RA septum, mid posterior RA, lateral RA, RAA anterior lateral, mitral annulus LA, posterior LA). The differences between smooth tissue with less resistance (RA septum, posterior RA, posterior LA, and mitral annulus with forces ranging between approximately 0 and 35 g and resistances between 98 and 135 Ohms) and pectinated tissue with higher resistance over a similar force range (lateral RA and RAA with forces ranging between approximately 3 and 58 g and resistances between 140 and 175 Ohms) are readily apparent.

Figure 7B:
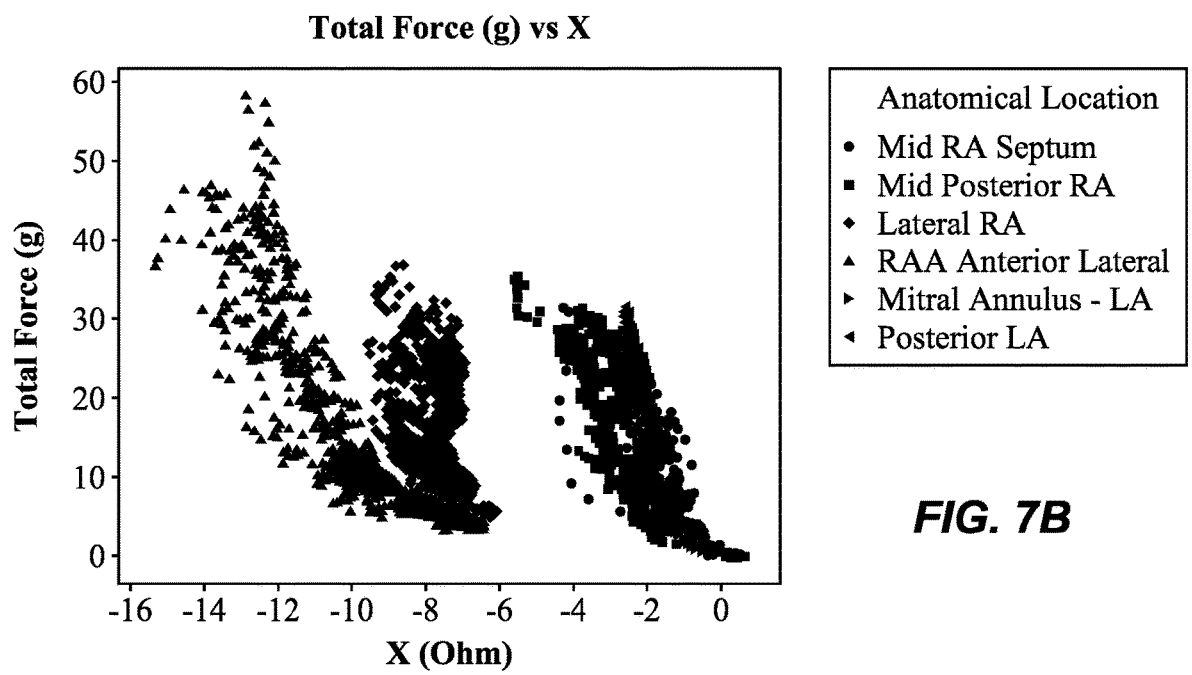

FIG. 7B illustrates the difference in force vs. reactance (X) data pairs when the catheter tip is in contact with different anatomical areas of the heart. Over a similar range of contact forces, the anterior/lateral right atrial appendage (RAA anterior lateral) has the greatest range in reactance (−15 to −6 Ohms) whereas the lateral RA has reactance values between −8 and −6 Ohms. The mid RA septum, mid posterior RA, mitral annulus LA, and posterior LA all have similar ranges of reactance values (forces between approximately 0 and 34 g and reactance between −6 and 1 Ohms).

Figure 7C:
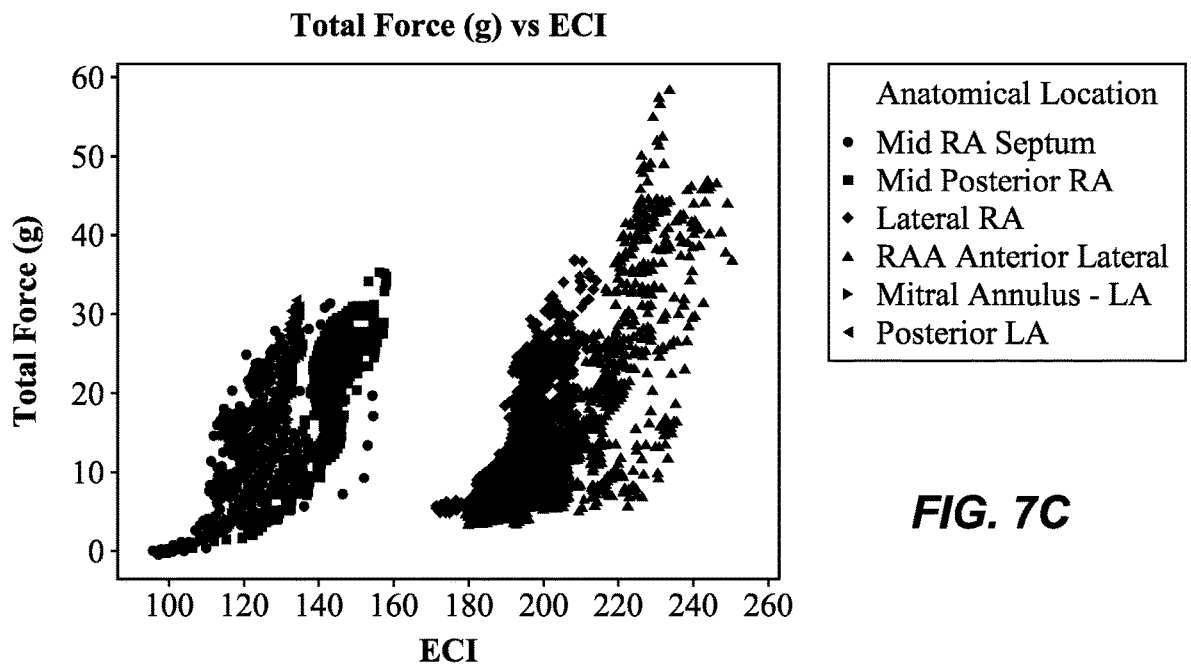

FIG. 7C illustrates the difference in force vs. ECI data pairs when the catheter tip is in contact with different anatomical areas of the heart (mid RA septum, mid posterior RA, lateral RA, RAA anterior lateral, mitral annulus LA, posterior LA). The mid RA septum, mid posterior RA, mitral annulus LA, and posterior LA all have similar ECI values (between approximately 95 and 160) over a similar force range (between approximately 0 and 35 g). Over a similar force range, the lateral RA has ECI values between 170 and 210. and the RAA anterior lateral has ECI values (ranging between 170 and 250).

Figure 7D:
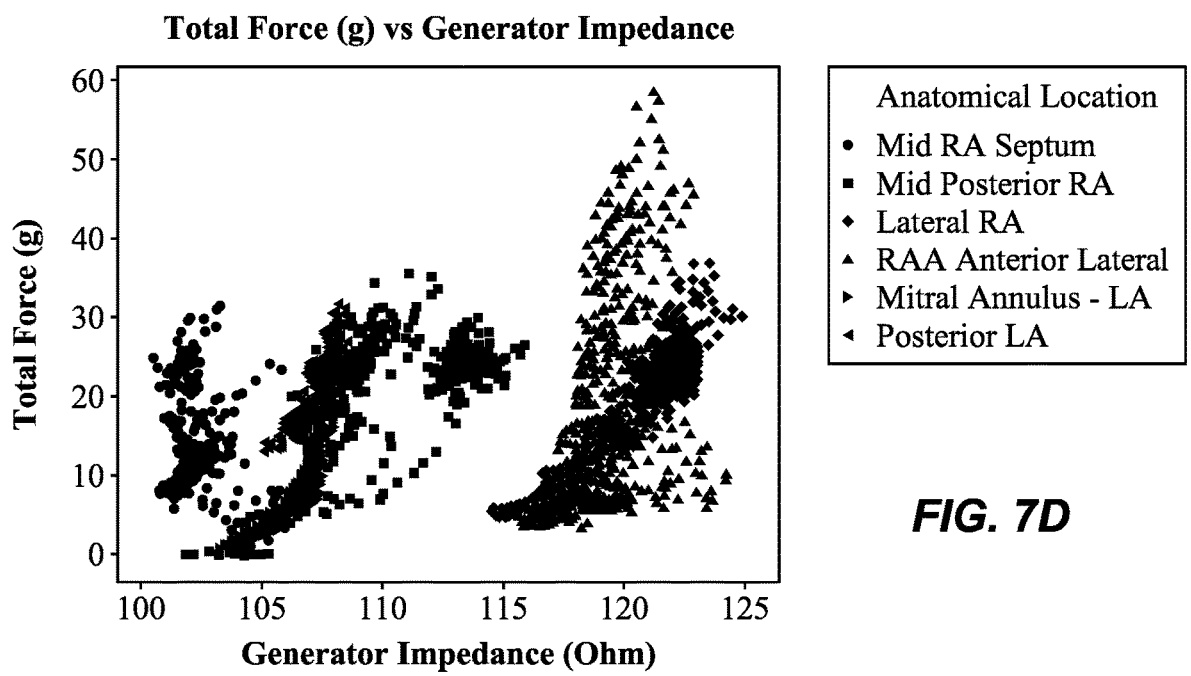

FIG. 7D illustrates the difference in force vs. RF generator impedance data pairs when the catheter tip is in contact with different anatomical areas of the heart. The mid RA septum, mid posterior RA, mitral annulus LA, and posterior LA all have generator impedance ranging from 100 to115 Ohms versus the lateral RA and RAA anterior lateral which range from 115 to 125 Ohms over a similar range of contact forces.

Figure 8A:
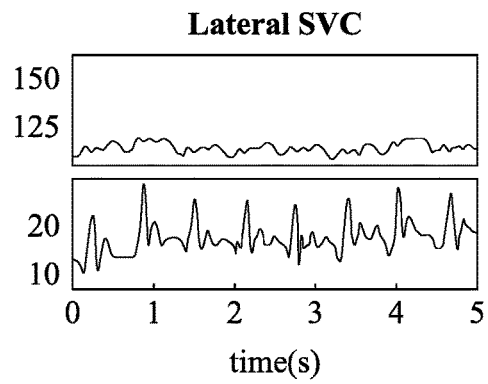
FIGS. 8A and 8B are line plots illustrating the time-based relationship between an electrical coupling index and contact force in an exemplary experimental procedure.

FIG. 8A depicts contact force values (in the lower portion of the graph) and ECI values (in the upper portion of the graph) collected during a first five second window of time at the lateral SVC. Similarly, FIG. 8B depicts contact force values (in the lower portion of the graph) and ECI values (in the upper portion of the graph) collected during a second five second window of time at the lateral right atrium during.

Figure 8B:
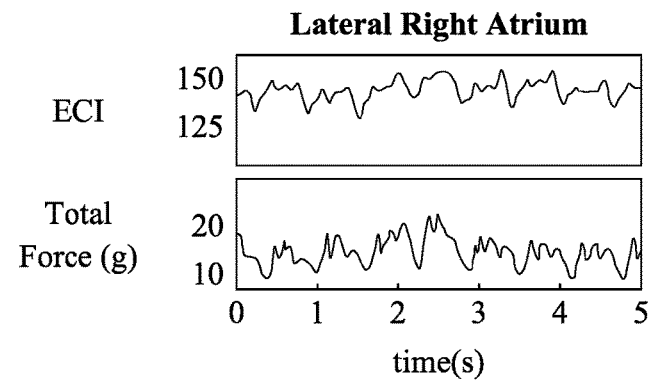
Figure 8C:
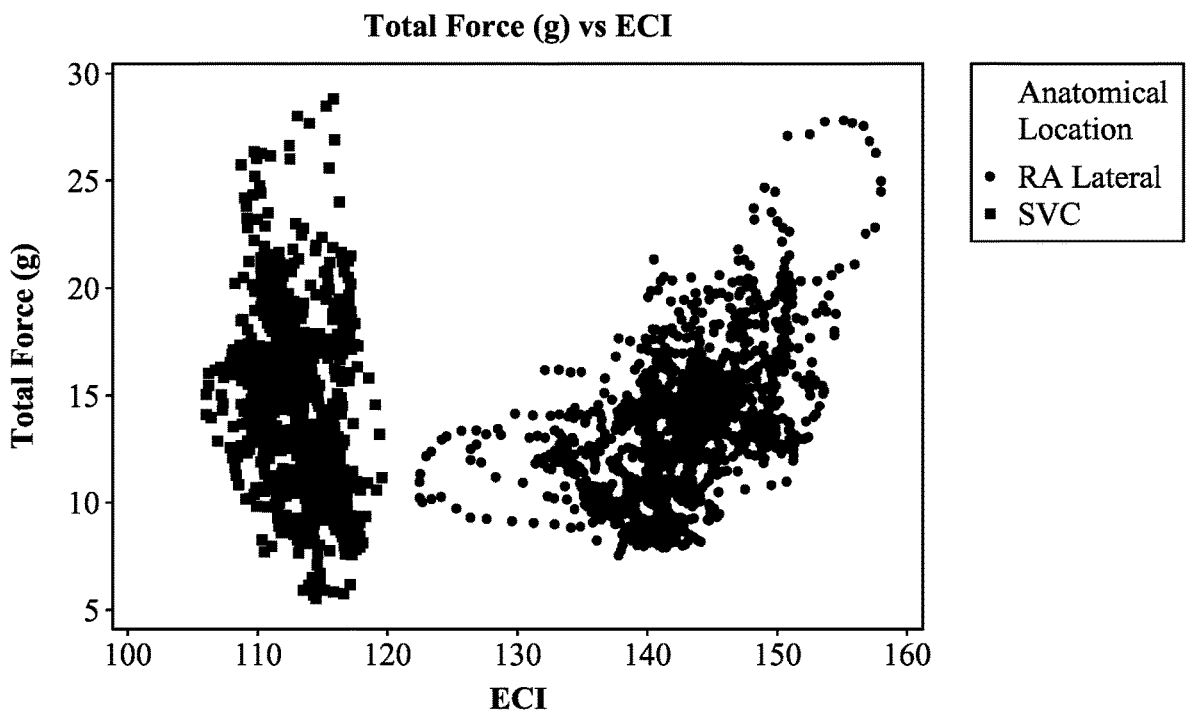
FIG. 8C is a scatter plot illustrating the relationship of total contact force and ECI for two different anatomical locations (lateral right atrium and superior vena cava (SVC)).

FIG. 8C illustrates a scatterplot of total force vs. ECI using the same data illustrated in FIGS. 8A and 8B. The scatterplot shows that the relationship between total contact force and ECI is clearly different in the two locations (SVC and lateral right atrium). The SVC and lateral right atrium (RA lateral) have similar total contact force values ranging between approximately 5 and 28 g. However, the ECI values for the SVC only range between approximately 100 and 120, whereas the lateral right atrium ECI values range between approximately 125 and 155.

Figure 9A:
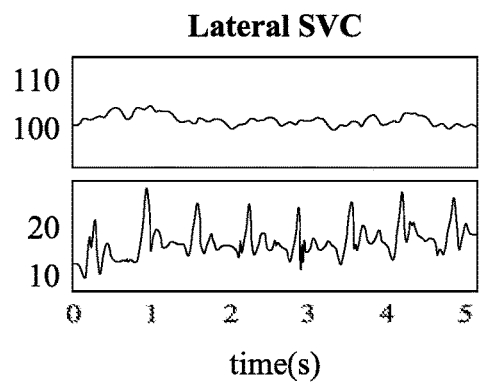
FIGS. 9A and 9B are line plots illustrating the time-based relationship between a simple impedance (e.g., generator impedance) and contact force in an exemplary experimental procedure.
Figure 9B:
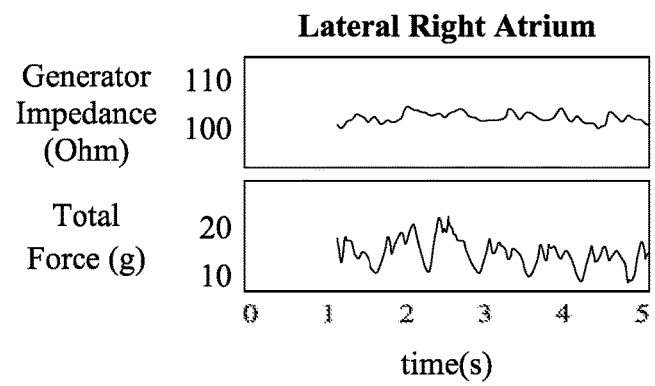

FIG. 9A depicts contact force values (in the lower portion of the graph) and generator impedance values (in the upper portion of the graph) collected during a first five second window of time at the lateral SVC. Similarly, FIG. 9B depicts contact force values (in the lower portion of the graph) and generator impedance values (in the upper portion of the graph) collected during a second five second window of time at the lateral right atrium. These recordings were taken simultaneous to those illustrated in FIG. 8.

Figure 9C:
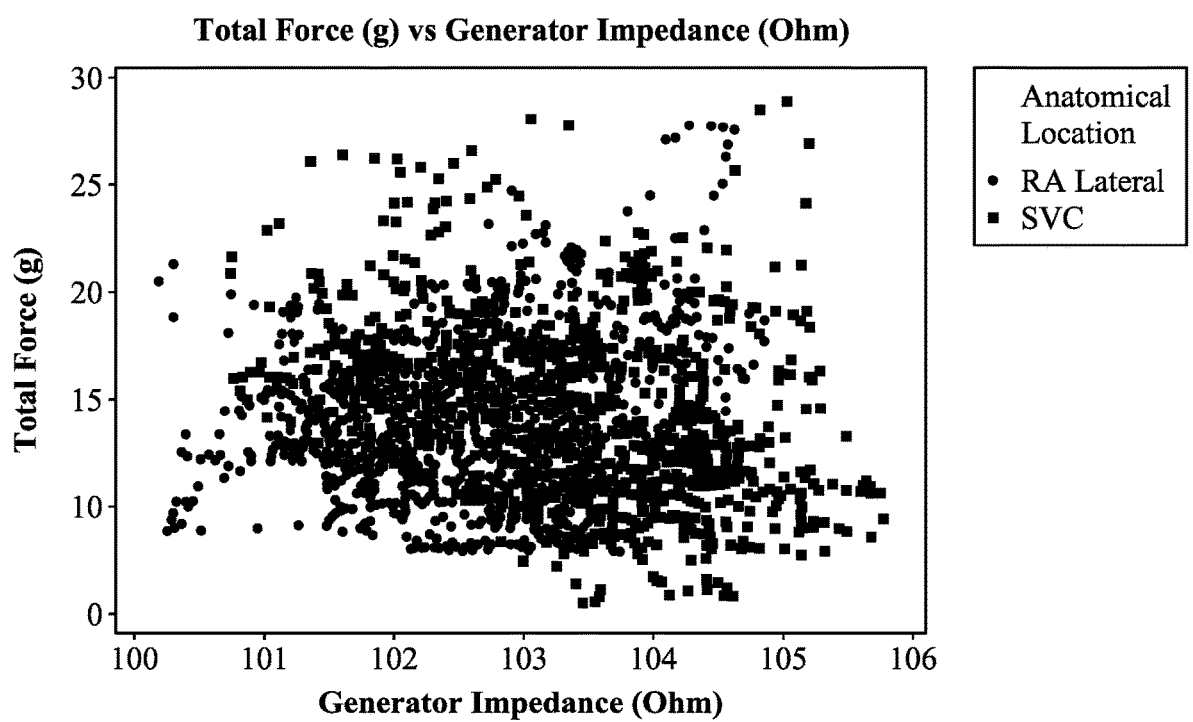
FIG. 9C is a scatter plot illustrating the relationship of total contact force and generator impedance I for two different anatomical locations (lateral right atrium and SVC).

FIG. 9C shows that the relationship between total contact force and generator impedance is not different in the two locations (SVC and lateral right atrium). Unlike the contact force vs. ECI relationship, the contact force vs. generator impedance relationship does not discriminate between these two anatomical locations. The SVC and lateral right atrium (RA lateral) have similar total contact force values ranging between approximately 5 and 28 g. similarly, the generator impedance values for the SVC and for the lateral right atrium similarly range between approximately 100 and 106.

Figure 10:
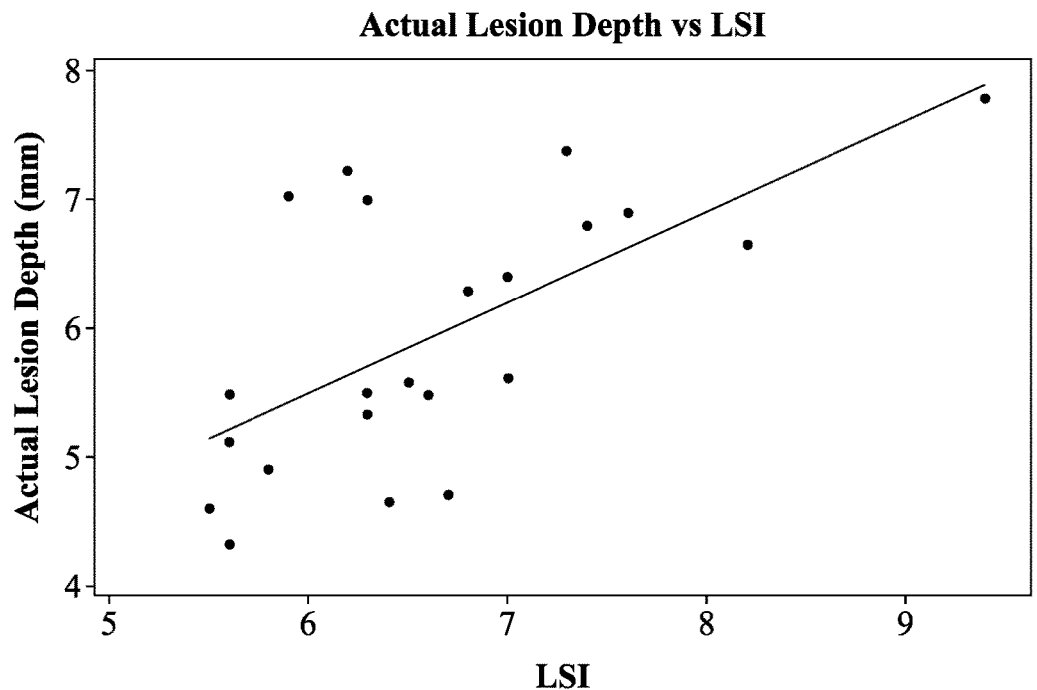
FIG. 10 is a scatter plot and best-fit line illustrating the relationship between a mathematically-predicted lesion size index, based on a lesion depth assessment, and an actual lesion depth in various exemplary experimental procedures.

FIG. 10 is an example of a relationship between actual lesion depth and LSI values. In FIG. 10, multiple linear regression analysis was completed correlating the measurements recorded from the various systems to the maximum RF ablation lesion depth. The first analysis included only the original LSI value, as reported by the TactiSys™ system. The $R^2$ for the relationship between actual RF lesion depth and LSI value was 0.41.

Figure 11:
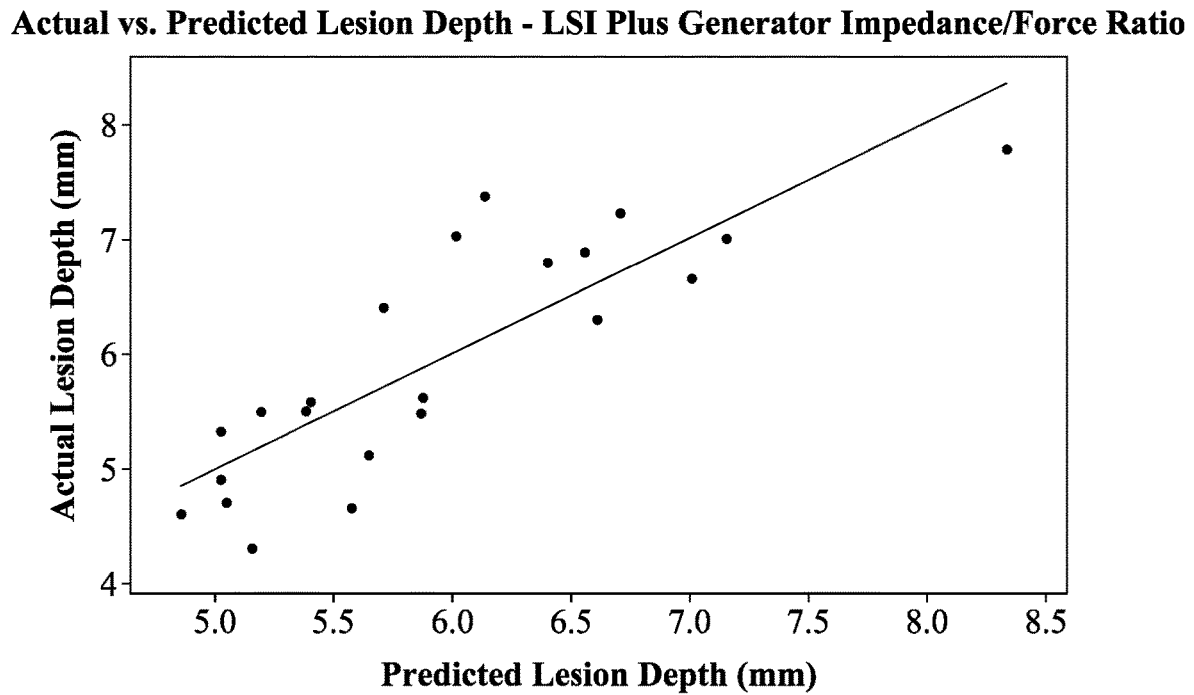
FIG. 11 is a scatter plot and best-fit line illustrating the relationship between a mathematically-predicted lesion size, based on a lesion depth assessment incorporating a ratio of an impedance to a contact force, and an actual lesion depth in various exemplary experimental procedures.
Figure 12:
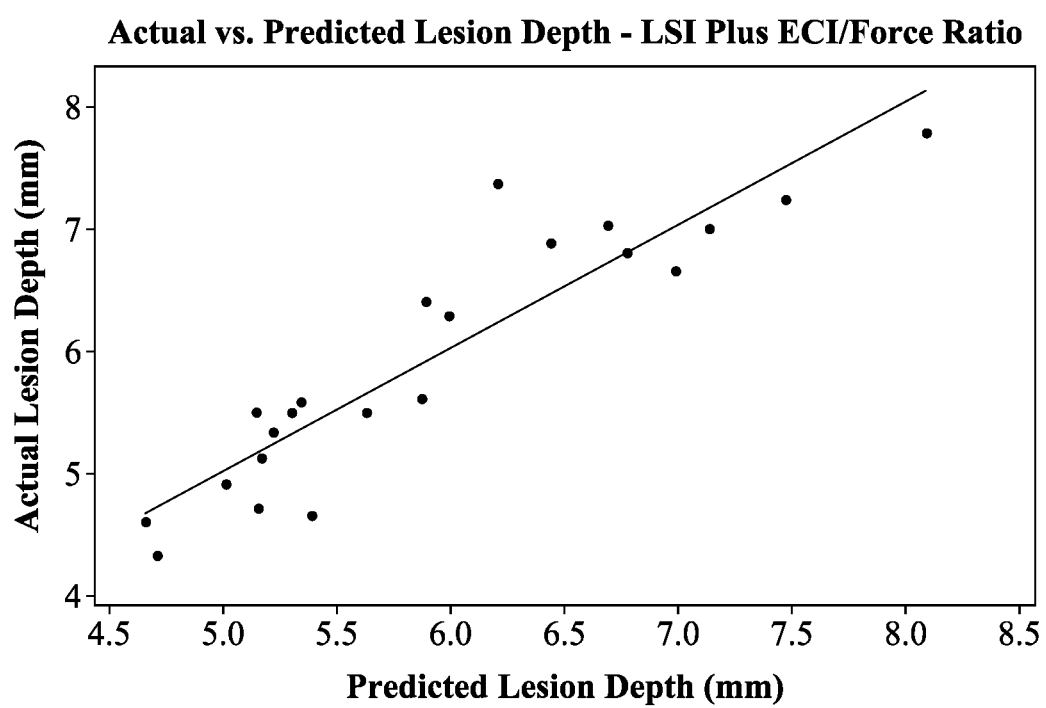
FIG. 12 is a scatter plot and best-fit line illustrating the relationship between a mathematically-predicted lesion size, based on a lesion depth assessment incorporating a ratio of an electrical coupling index to a contact force, and an actual lesion depth in various exemplary experimental procedures.

FIG. 11 depicts the relationship between actual lesion depth and predicted lesion depth. In this example, the predicted lesion depth is based upon the LSI value in combination with a ratio of RF generator impedance value to total force. Equation (9) below defines the line depicted in FIG. 11:

$$\text{depth} = -5.49 + 1.41 * LSI + 0.210 * \left(\frac{Z}{TF}\right) \tag{9}$$

In equation (9), the LSI value is the lesion index provided by the TactiSys™ system, Z is the 1 second average of generator impedance 0.5 seconds after the onset of ablation provided by the RF generator, and TF is the total force (e.g., contact force between the catheter tip and tissue) from the TactiSys™ system at the same time point. The correlation between actual lesion depth and equation (9) predicted lesion depth resulted in an $R^2$ of 0.706.

FIG. 12 again depicts the relationship between actual lesion depth and predicted lesion depth. In this example, however, the predicted lesion depth is based upon the LSI value in combination with a ratio of the ECI value to total force. Equation (10) below defines the line depicted in FIG. 12:

$$depth = -2.87 + 1.12 * LSI + 0.0594 * \left(\frac{ECI}{TF}\right) \quad (10)$$

In equation (9), the LSI value is the lesion size index provided by the TactiSys™ system, ECI is the 1 second average of the ECI value 0.5 seconds after the onset of ablation, and TF is the total force (e.g., contact force between the catheter tip and tissue) from the TactiSys™ system at the same time point. The correlation between actual lesion depth and equation (10) predicted lesion depth resulted in an $R^2$ of 0.842.

Figure 13:
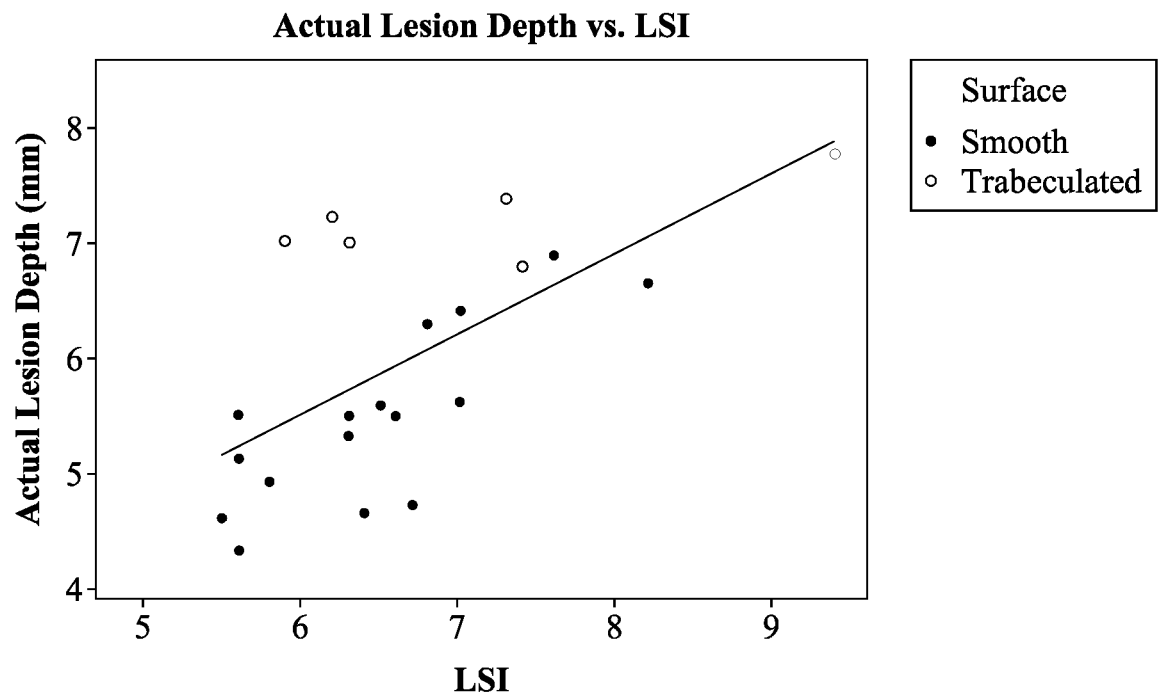
FIG. 13 is a scatter plot and best-fit line illustrating the relationship between actual lesion depth and LSI.
Figure 14:
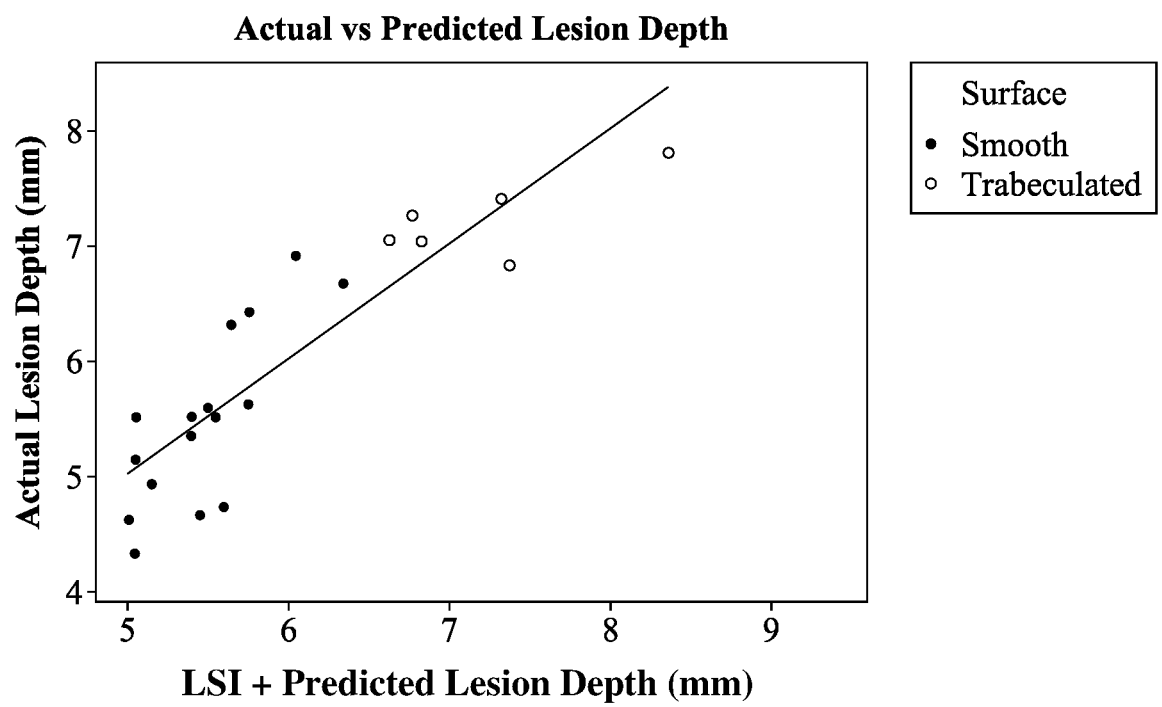
FIG. 14 depicts a best-fit line over a scatter plot showing the relationship between actual lesion depth and a mathematically-predicted lesion depth (using LSI in this example) for two types of tissue (smooth or trabeculated).

The degree of electrical coupling with the cardiac tissue, at a given contact force, is expected to be greater when the ablation catheter is in contact with trabeculated tissue compared to contact with smooth tissue. In addition, with all else being equal, larger lesions will be formed when there is larger electrical coupling between, for example, the ablation tip electrode 17 and the cardiac tissue 16. FIG. 13 (similar to FIG. 10) and FIG. 14 illustrates the improvement to the relationship between actual lesion depth and LSI when tissue surface morphology (e.g., smooth vs. trabeculated, as classified during the experiment) is considered along with LSI using linear regression analysis. When correlating to actual lesion depth, addition of tissue surface morphology to LSI provided an $R^2=0.77$ compared to 0.41 for LSI alone (as noted above).

Figure 15:
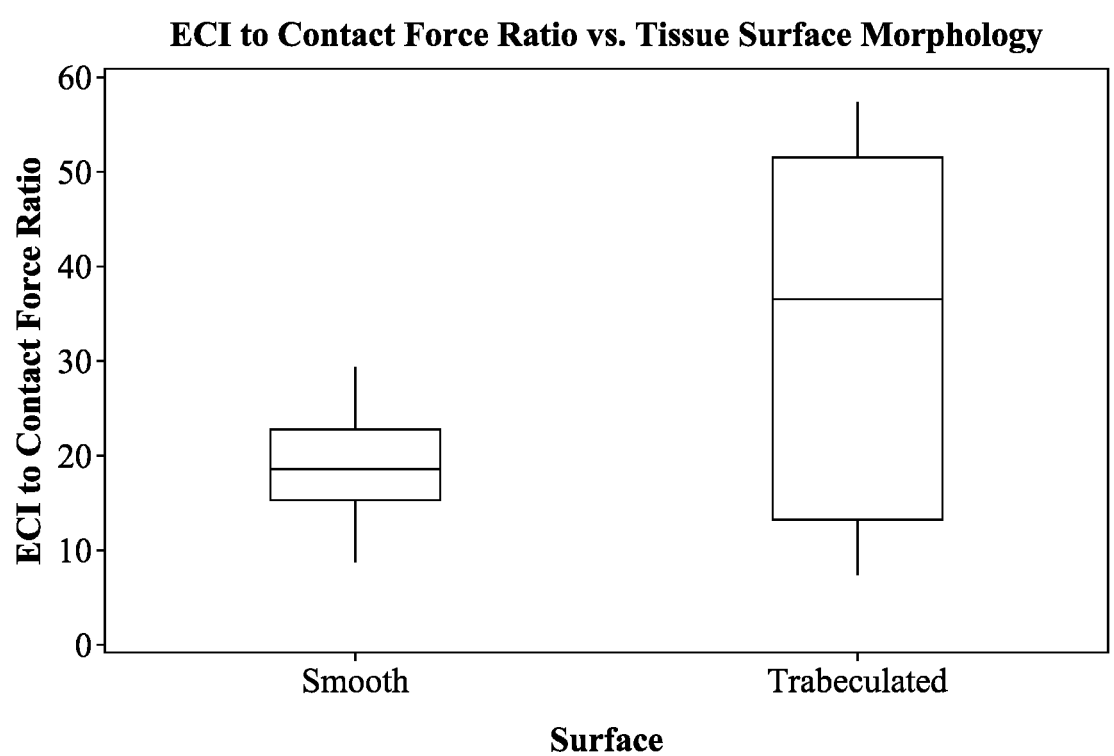
FIG. 15 is a plot illustrating exemplary ranges of a ratio between an electrical coupling index to a contact force for smooth and trabeculated tissue types.

As stated elsewhere herein, the ratio of ECI or RF generator impedance to contact force provides a surrogate for tissue surface morphology. FIG. 15 demonstrates the relationship between surface morphology and the ratio of ECI to contact force. In particular, as shown on the left-hand portion FIG. 15, the ratio of ECI to contact force does not vary much for smooth tissue, and the ratio of ECI to contact force varies more dramatically for trabeculated tissue.

Although LSI accounts for RF current, duration, and contact force when predicting RF ablation lesion size, it does not account for important morphological variations which may be present in cardiac tissue. Tissue morphological differences can influence RF lesion size predictability.

Although numerous embodiments of this invention have been described above with a certain degree of particularity, those skilled in the art could make numerous alterations to the disclosed embodiments without departing from the spirit or scope of this disclosure. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the any aspect of the disclosure. As used herein, the phrases "configured to," "configured for," and similar phrases indicate that the subject device, apparatus, or system is designed and/or constructed (e.g., through appropriate hardware, software, and/or components) to fulfill one or more specific object purposes, not that the subject device, apparatus, or system is merely capable of performing the object purpose. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

What is claimed is:

1. A method for delivering ablation energy to tissue of a patient comprising: receiving or determining a measure of impedance between an electrode and the tissue of the patient; receiving or determining a measure of contact force between the electrode and the tissue; characterizing the tissue based on a ratio of the measure of impedance between the electrode and the tissue to the measure of contact force, wherein the ratio of the measure of impedance between the electrode and the tissue to the measure of contact force comprises a fraction in which a value of the measure of impedance is one of the numerator or the denominator and a value of the measure of contact force is the other of the numerator or denominator; causing the tissue characterization to be presented to a user, or applying the tissue characterization to calculate a metric and causing the metric to be presented to the user; and using the tissue characterization to control the delivery of the ablation energy to the tissue of the patient.

2. The method of claim 1, wherein the measure of impedance comprises a complex impedance and the fraction comprises a fraction in which a metric calculated from at least a resistance and a reactance of the complex impedance or a magnitude and a phase angle of the complex impedance is one of the numerator or denominator and the value of the measure of contact force is the other of the numerator and denominator.

3. The method of claim 1, further comprising causing the tissue characterization to be presented to a user by causing the tissue characterization to be displayed.

4. The method of claim 1, further comprising causing the tissue characterization to be presented to a user by adding the tissue characterization to a map or model of the tissue and causing the map or model of the tissue to be displayed.

5. The method of claim 1, further comprising applying the tissue characterization to calculate the metric, wherein the metric is indicative of a size of a lesion in the tissue.

6. The method of claim 5, further comprising:
receiving or determining a measure of energy applied between the electrode and the tissue; and
calculating the metric according to the measure of energy applied, the measure of contact force, and the ratio of the measure of impedance between the electrode and the tissue to the measure of contact force.

7. A method for applying energy to tissue of a patient comprising: receiving or determining a measure of energy applied from an electrode to the tissue of the patient; receiving or determining a measure of an impedance between the electrode and the tissue; receiving or determining a measure of contact force between the electrode and the tissue; calculating a ratio of the measure of impedance to the measure of contact force, where the measure of impedance is the denominator and the measure of contact force is the numerator, wherein the impedance is a complex impedance and wherein the denominator of the ratio is calculated based on at least a reactance and a resistance of the complex impedance, or a magnitude and a phase angle of the complex impedance; calculating a size of a lesion in the tissue according to the measure of energy applied and the ratio of the measure of impedance to the measure of contact force; displaying the lesion size to a clinician; and using the lesion size to control the application of the energy from the electrode to the tissue of the patient.

8. The method according to claim 7, wherein receiving or determining the measure of energy applied comprises measuring instantaneous power and a duration of energy application, and wherein calculating the size of the lesion comprises calculating the size of the lesion according to the measure of instantaneous power, the duration of energy application, and the ratio of impedance and force.

9. The method according to claim 7, wherein displaying lesion size to the clinician comprises causing the lesion size to be presented to a user by adding a lesion depth to a map or model of the tissue and causing the model to be displayed.

10. The method according to claim 9, wherein the lesion size is indicative of one or more of the depth, a width, and a volume of the lesion.

11. A method for delivering ablation therapy to target tissue of a patient comprising: measuring electrical parameters at an interface between an electrode and the target tissue of the patient; measuring contact force between the electrode and the target tissue via a force sensor; measuring energy applied from the electrode to the target tissue during the ablation therapy; determining lesion size index according to an equation $$LSI(F, I, t) = k_1\left(f_2\left(1 - e^{-F/f_1}\right) + f_0\right) * i_2\left(1 - e^{-(I/i_1)^2}\right) * \left[(1 - k_0) + k_0 \frac{1 - e^{-t/\tau}}{1 - e^{-T/\tau}}\right],$$

where F is force in grams, I is current in milliamps, t is a time in seconds, fo, f1, and f2 are force parameter coefficients, i1 and i2 are electrical current coefficients, ko is a diffusive heating coefficient, ki is a rescaling coefficient, T is a characteristic time value, and the output LSI is in millimeters; determining electrical coupling index, based upon at least one of the determined lesion size index, electrical coupling index and measured energy; characterizing the tissue, based upon at least one of the determined lesion size index, electrical coupling index and measured energy; predicting lesion size and depth of the ablation therapy; outputting the tissue characterization and lesion size and depth to a clinician; and using the tissue characterization and lesion size and depth to control the application of energy from the electrode to the target tissue of the patient during the ablation therapy.

12. The method according to claim 11, wherein the electrical parameters comprise a complex impedance.

13. The method according to claim 12, wherein the electrical coupling index is calculated in accordance with an equation $$ECI = a*\overline{R} + b*\overline{X} + c,$$

where $\overline{R}$ and $\overline{X}$ are the mean values of a resistance and reactance of the complex impedance, respectively, and a, b, and c are experimentally-determined coefficients associated with the specific equipment used for measurement.

* * * * *